(12) United States Patent
Buchine et al.

(10) Patent No.: US 12,239,823 B2
(45) Date of Patent: Mar. 4, 2025

(54) DRUG MIXING AND DELIVERY SYSTEM AND METHOD

(71) Applicant: Windgap Medical, Inc., Watertown, MA (US)

(72) Inventors: Brent A. Buchine, Austin, TX (US); Adam R. Standley, Cambridge, MA (US); Christopher J. Stepanian, Somerville, MA (US)

(73) Assignee: Windgap Medical, Inc., Watertown, MA (US)

( * ) Notice: Subject to any disclaimer, the term of this patent is extended or adjusted under 35 U.S.C. 154(b) by 0 days.

(21) Appl. No.: 17/991,676

(22) Filed: Nov. 21, 2022

(65) Prior Publication Data

US 2023/0088439 A1    Mar. 23, 2023

Related U.S. Application Data

(63) Continuation of application No. 14/576,179, filed on Dec. 18, 2014, now abandoned.
(Continued)

(51) Int. Cl.
*A61M 5/24* (2006.01)
*A61K 9/00* (2006.01)
(Continued)

(52) U.S. Cl.
CPC .......... *A61M 5/2448* (2013.01); *A61K 9/0019* (2013.01); *A61K 31/137* (2013.01); *A61K 31/4045* (2013.01); *A61K 38/26* (2013.01); *A61K 45/06* (2013.01); *A61M 5/1409* (2013.01); *A61M 5/19* (2013.01); *A61M 5/2046* (2013.01); *A61M 5/284* (2013.01); *A61M 5/3294* (2013.01); *A61M 5/44* (2013.01);
(Continued)

(58) Field of Classification Search
CPC ................ A61K 9/0019; A61K 31/137; A61K 31/4045; A61K 38/26; A61K 45/06; A61K 38/00; A61M 5/1409; A61M 5/19; A61M 5/2046; A61M 5/284; A61M 5/3294; A61M 5/44; A61M 2205/364; A61M 2205/366
See application file for complete search history.

(56) References Cited

U.S. PATENT DOCUMENTS

| 4,147,767 A | 4/1979 | Yapel |
| 4,479,794 A | 10/1984 | Urquhart et al. |

(Continued)

FOREIGN PATENT DOCUMENTS

| CN | 1634002 A | 7/2005 |
| CN | 1827109 A | 9/2006 |

(Continued)

OTHER PUBLICATIONS

Supplementary European Search Report for European Patent Application No. EP 14 872 735.7 mailed on Aug. 23, 2017.
(Continued)

*Primary Examiner* — Trevor Love
(74) *Attorney, Agent, or Firm* — Wolf, Greenfield & Sacks, P.C.

(57) ABSTRACT

The present disclosure provides methods of preparing a medical solution. In some aspects, the medical solution can be prepared from mixing a first liquid with a second liquid or mixing a solid component with a liquid in an autoinjector. In some aspects, the heat released from the mixing can promote solubility of a dry medicament in the solution.

13 Claims, 12 Drawing Sheets

Related U.S. Application Data

(60) Provisional application No. 62/016,260, filed on Jun. 24, 2014, provisional application No. 61/917,925, filed on Dec. 18, 2013.

(51) Int. Cl.
  *A61K 31/137* (2006.01)
  *A61K 31/4045* (2006.01)
  *A61K 38/00* (2006.01)
  *A61K 38/26* (2006.01)
  *A61K 45/06* (2006.01)
  *A61M 5/14* (2006.01)
  *A61M 5/19* (2006.01)
  *A61M 5/20* (2006.01)
  *A61M 5/28* (2006.01)
  *A61M 5/32* (2006.01)
  *A61M 5/44* (2006.01)

(52) U.S. Cl.
  CPC ........ *A61K 38/00* (2013.01); *A61M 2205/364* (2013.01); *A61M 2205/366* (2013.01)

(56) References Cited

U.S. PATENT DOCUMENTS

| | | | |
|---|---|---|---|
| 4,511,351 A | 4/1985 | Theeuwes | |
| 4,755,169 A | 7/1988 | Sarnoff et al. | |
| 4,820,286 A | 4/1989 | van der Wal | |
| 6,641,561 B1 | 11/2003 | Hill et al. | |
| 6,656,150 B2 | 12/2003 | Hill et al. | |
| 6,770,052 B2 | 8/2004 | Hill et al. | |
| 6,793,646 B1 | 9/2004 | Giambattista et al. | |
| 6,953,455 B2 | 10/2005 | Cho et al. | |
| 7,323,477 B2 | 1/2008 | Chow et al. | |
| 7,449,012 B2 | 11/2008 | Young et al. | |
| 7,544,189 B2 | 6/2009 | Griffiths | |
| 7,556,614 B2 | 7/2009 | Griffiths et al. | |
| 7,608,055 B2 | 10/2009 | Griffiths et al. | |
| 7,621,887 B2 | 11/2009 | Griffiths et al. | |
| 7,678,073 B2 | 3/2010 | Griffiths et al. | |
| 7,749,190 B2 | 7/2010 | Griffiths et al. | |
| 7,757,370 B2 | 7/2010 | Griffiths | |
| 7,776,015 B2 | 8/2010 | Sadowski et al. | |
| 7,794,432 B2 | 9/2010 | Young et al. | |
| 7,947,742 B2 | 5/2011 | Batycky et al. | |
| 8,048,035 B2 | 11/2011 | Mesa et al. | |
| 8,057,427 B2 | 11/2011 | Griffiths et al. | |
| 8,092,420 B2 | 1/2012 | Bendek et al. | |
| 8,123,719 B2 | 2/2012 | Edwards et al. | |
| 8,177,758 B2 | 5/2012 | Brooks, Jr. et al. | |
| 8,187,220 B2 | 5/2012 | Griffiths et al. | |
| 8,251,947 B2 | 8/2012 | KraMer et al. | |
| 8,313,466 B2 | 11/2012 | Edwards et al. | |
| 8,496,619 B2 | 7/2013 | Kramer et al. | |
| 8,506,526 B2 | 8/2013 | Griffiths et al. | |
| 8,568,367 B2 | 10/2013 | Griffiths et al. | |
| 8,613,720 B2 | 12/2013 | Bendek et al. | |
| 8,632,504 B2 | 1/2014 | Young | |
| 8,696,618 B2 | 4/2014 | Kramer et al. | |
| 8,770,827 B2 | 7/2014 | Steinmuller et al. | |
| 8,945,053 B2 | 2/2015 | Vogt et al. | |
| 9,364,610 B2 | 6/2016 | KraMer et al. | |
| 9,364,611 B2 | 6/2016 | KraMer et al. | |
| 9,586,010 B2 | 3/2017 | Mesa et al. | |
| 11,246,842 B2 | 2/2022 | Standley et al. | |
| 2003/0187388 A1 | 10/2003 | Sharon et al. | |
| 2004/0076588 A1 | 4/2004 | Batycky et al. | |
| 2004/0110781 A1 | 6/2004 | Harmon et al. | |
| 2005/0281883 A1 | 12/2005 | Daniloff et al. | |
| 2006/0257488 A1 | 11/2006 | Hubbard | |
| 2007/0203247 A1 | 8/2007 | Phillips et al. | |
| 2008/0269347 A1 | 10/2008 | Bruss et al. | |
| 2010/0179090 A1 | 7/2010 | Havelund et al. | |
| 2011/0092906 A1 | 4/2011 | Bottger et al. | |
| 2011/0092917 A1 | 4/2011 | Wei et al. | |
| 2012/0016296 A1 | 1/2012 | Charles | |
| 2012/0046225 A1 | 2/2012 | Prestrelski et al. | |
| 2012/0130318 A1 | 5/2012 | Young | |
| 2013/0018313 A1 | 7/2013 | Dede | |
| 2013/0178823 A1 | 7/2013 | Buchine et al. | |
| 2014/0088512 A1 | 3/2014 | Quinn | |
| 2014/0276385 A1 | 9/2014 | Buchine et al. | |
| 2014/0276430 A1 | 9/2014 | Baker et al. | |
| 2015/0011975 A1 | 1/2015 | Anderson et al. | |
| 2015/0231334 A1 | 8/2015 | Buchine et al. | |
| 2016/0243060 A1 | 8/2016 | Standley et al. | |

FOREIGN PATENT DOCUMENTS

| | | |
|---|---|---|
| CN | 101674812 A | 3/2010 |
| CN | 102389403 A | 3/2012 |
| CN | 102497882 A | 6/2012 |
| CN | 102802668 A | 11/2012 |
| CN | 103442695 A | 12/2013 |
| CN | 106061253 A | 10/2016 |
| FR | 2741810 A1 | 6/1997 |
| JP | 2010-526039 A | 7/2010 |
| JP | 2012-528830 A | 11/2012 |
| JP | 2013-500952 A | 1/2013 |
| JP | 55-31075 B2 | 6/2014 |
| JP | 2014-523296 A | 9/2014 |
| WO | WO 2000/48662 A1 | 8/2000 |
| WO | WO 2000/66214 A1 | 11/2000 |
| WO | WO 2002/41830 A2 | 5/2002 |
| WO | WO 2003/047663 A2 | 6/2003 |
| WO | WO 2007/057717 A2 | 5/2007 |
| WO | WO 2008/132224 A1 | 11/2008 |
| WO | WO 2010/139751 A2 | 12/2010 |
| WO | WO 2010/139752 A2 | 12/2010 |
| WO | WO 2011/012719 A1 | 2/2011 |
| WO | WO 2012/122535 A2 | 9/2012 |
| WO | WO 2012/177948 A2 | 12/2012 |
| WO | WO 2014/026694 A1 | 2/2014 |
| WO | WO 2014/059444 A2 | 4/2014 |
| WO | WO 2014/060563 A2 | 4/2014 |
| WO | WO 2014/066731 A1 | 5/2014 |
| WO | WO 2014/146060 A1 | 9/2014 |
| WO | WO 2014/205463 A1 | 12/2014 |
| WO | WO 2015/095624 A2 | 6/2015 |
| WO | WO 2019/011069 A1 | 1/2019 |

OTHER PUBLICATIONS

International Search Report and Written Opinion for International Application No. PCT/US14/71324 mailed Sep. 2, 2015.
International Preliminary Report on Patentability for International Application No. PCT/US14/71324 mailed Jun. 30, 2016.
Supplementary European Search Report for European Patent Application No. EP 15 871 257.0 mailed on Jul. 11, 2018.
International Search Report and Written Opinion for International Application No. PCT/US2015/066940 mailed Feb. 25, 2016.
International Preliminary Report on Patentability for International Application No. PCT/US2015/066940 mailed on Jun. 29, 2017.
[No Author Listed], Addrenalin (epinephrine injection) 1 mg/mL (1:1000). JHP Pharmaceuticals, LLC. Dec. 2012. <URL: https://www.accessdata.fda.gov/drugsatfda_docs/label/2012/204200s000lbl.pdf> [retrieved from internet on Feb. 1, 20211] 10 pages.
[No Author Listed], Epinephrine Injection USP, Material Data Sheet. Luitpold Pharmaceuticals, Inc. Jan. 10, 2009. <URL: https://marketing.msdsonline.com/library/ioj/ioj708.pdf > retrieved from internet on Feb. 11, 2021] 8 pages.
Kerddonfak et al., The stability and sterility of epinephrine prefilled syringe. Asian Pac J Allergy Immunol. Mar. 2010;28(1):53-7.
Alvarez-Perea et al., Advancements in Anaphylaxis Management. Curr Pharm Des. 2023;29(3):185-195. doi: 10.2174/1381612829666221021150946.
Bansal, Product Development Issues of Powders for Injection. Mar. 2002. Last accessed on Feb. 27, 2017 from https://www.researchgate.net/profile/Arvind_Bansal/publication/228912123_Product_development_issues_of_powder_for_injection/links/

(56) References Cited

OTHER PUBLICATIONS

55e43bc808aecb1a7cc8fa.pdf. 12 pages.

Landy et al., An open-label trial of a sumatriptan auto-injector for migraine in patients currently treated with subcutaneous sumatriptan. Headache. Jan. 2013;53(1):118-125. doi: 10.1111/j.1526-4610.2012.02295.x. Epub Nov. 13, 2012.

Parish et al., A systematic review of epinephrine degradation with exposure to excessive heat or cold. Ann Allergy Asthma Immunol. Jul. 2016; 117(1):79-87. doi: 10.1016/j.anai.2016.04.006. Epub May 21, 2016.

Shaker et al., An update on the impact of food allergy on anxiety and quality of life. Curr Opin Pediatr. Aug. 2017;29(4):497-502. doi: 10.1097/MOP.0000000000000509.

Two-step mixing and Injection Process

DRUG MIXING AND DELIVERY SYSTEM AND METHOD

RELATED APPLICATIONS

This application is a continuation of U.S. patent application Ser. No. 14/576,179, filed Dec. 18, 2014, which claims priority under 35 U.S.C. § 119 (e) to U.S. Provisional Patent Application No. 61/917,925, filed Dec. 18, 2013, and U.S. Provisional Patent Application No. 62/016,260, filed Jun. 24, 2014, each of which is incorporated herein by reference in its entirety.

BACKGROUND OF INVENTION

Individuals who suffer from certain medical conditions are often required to keep an auto-injector or prefilled syringe nearby in order to address a medical need. A few examples of this are insulin pens for people with diabetes, epinephrine autoinjectors for those with food and insect stings allergies, and antidotes for soldiers at risk of exposure to chemical and/or biological toxins in the field.

Exposure to certain substances, such as, for example, peanuts, shellfish, bee venom, certain drugs, toxins, and the like, can cause allergic reactions in sensitive individuals. Such allergic reactions can lead to anaphylactic shock. This can cause a sharp drop in blood pressure, hives, and/or severe airway constriction and can be a life-threatening condition. The response of a sensitive individual to an allergen can either gradually or abruptly increase or decrease over time, making a large portion of those sensitive individuals needful of a solution to mitigate the effects of anaphylactic shock. Responding rapidly to mitigate the effects from such exposures can prevent injury and/or death. For example, in certain situations, an injection of epinephrine (i.e., adrenaline) can provide substantial and/or complete relief from the allergic reaction.

With regards to allergies, for example, an allergic reaction may occur in a location physically distant from the nearest hospital or medical facility. For example, bee stings are more likely to occur outside than indoors. Food containing peanuts are more likely to be supplied to the individual away from a controlled home environment like at a baseball park.

Because emergency medical facilities may not be available when an individual is suffering from an allergic reaction, some individuals carry a medicament delivery device, such as, for example, an auto-injector, to rapidly self-administer the epinephrine in response to an allergic reaction. Having an epinephrine auto-injector nearby enables emergency intervention after an exposure to an allergen to reduce and/or reverse the side-effects of life threatening anaphylaxis.

For patients that are required to carry epinephrine auto-injectors with them, the thermal stability profile of the medication can present an issue. Patients must care for their medications in a way that prevents them from being exposed to excessive heat or cold outside of controlled room temperature. Not doing so can degrade the medication rapidly and result in a drug that doesn't have the recommended potency to deal with the onsets of anaphylactic shock.

SUMMARY

In some embodiments, aspects of the invention relate to dry drug compositions (e.g., dry powder compositions) that can be dissolved and/or reconstituted rapidly for delivery to a patient (e.g., a human patient). According to aspects of the invention, dry compositions have several advantages over liquid compositions, including increased stability (e.g., a long shelf life, potency and/or chiral stability) over time and upon exposure to changes in temperature.

In some embodiments, a dry drug composition comprises an epinephrine free base. In some embodiments the dry drug composition comprises an L-epinephrine freebase. In some embodiments, a dry drug composition comprises an epinephrine salt. In some embodiments, the epinephrine salt is a maleate, malate, fumarate, acid tartrate, hydrogen tartrate, or sulfate salt of epinephrine. In some embodiments, the epinephrine salt is epinephrine hydrochloride. In some embodiments, the epinephrine salt is epinephrine bitartrate. In some embodiments, the epinephrine salt is epinephrine borate. In some embodiments, the epinephrine is L-epinephrine. In some embodiments, the dry drug composition further comprises a salt and/or an antioxidant. In some embodiments, the dry drug composition comprises sodium metabisulfite and/or manitol.

In some embodiments, a dry drug composition is prepared by drying a drug solution (e.g., by vacuum drying, freeze drying, lyophilizing, or any suitable drying technique, as aspects of the invention are not limited in this respect). In some embodiments the dry drug is placed inside the auto-injector as a dry powder. In some embodiments, a dry composition may have any suitable particle size that allows for efficient and rapid reconstitution. In some embodiments, the particle size of the dry drug can be controlled by drying a drug solution within a confined volume. For example, in some embodiments, a drug solution is dried within the confines of an autoinjector (e.g., within one or more microfluidic channels of an autoinjector). As a result, the particle size of a dried drug composition may be one the order of the diameter of a microfluidic channel (e.g., from about 1 micron to about 500 microns in diameter). However, smaller or larger particle sizes may be used in some embodiments.

It should be appreciated that a dried drug composition may include the drug alone and/or any other molecules that were present in the drug solution (e.g., one or more salts, stabilizers, anti-oxidants, etc., or any combination thereof).

It also should be appreciated that the composition can be dried to different extents depending on the conditions used and the nature of the composition (e.g., the drug and other components of the composition). In some embodiments, a dry composition has less than 50% water by weight, less than 40% water by weight, less than 30% water by weight, less than 20% water by weight, less than 10% water by weight, less than 5% water by weight, less than 1% water by weight, less than 0.1% water by weight, less than 0.01% water by weight, or less.

It also should be appreciated that a dry drug composition can be dissolved and/or mixed and/or reconstituted by exposure to water or any suitable solvent (aqueous or non-aqueous), with or without salts and/or other buffers or components.

Accordingly, in some embodiments, the present disclosure provides pharmaceutical compositions comprising a medicament as a dry component. The medicament can be kept out of the liquid phase and stored as a dry medication, for example, as a lyophilized, spray dried, vacuum dried or chemical derived powder. The dry medicament has the advantages of an extended shelf-life, reduced temperature susceptibility, a greater efficacy and potency to endure over a longer period of time and through a wider range of temperature environments.

In some embodiments, aspects of the invention relate to a sealed container comprising a dry drug composition (e.g., a dry drug powder) as described herein. In some embodiments, the sealed container is incorporated into the housing of an injector. In some embodiments, the sealed container is a microfluidic channel in an injector and wherein the channel is connected to a liquid reservoir. In some embodiments the dry drug is placed inside the microfluidic channel.

In some embodiments, aspects of the invention relate to an injector comprising a dry drug composition.

In some embodiments, dry drug compositions can be prepared and/or delivered in injector devices. In some embodiments, an injector device also contains a liquid reservoir that can be accessed to deliver a fluid to the dry composition in order to solubilize and/or rehydrate and/or dissolve the drug immediately prior to injection. In some embodiments, the injector is an autoinjector that automatically mixes the dry drug composition with the fluid when the injector is activated.

In some embodiments the dry drug is placed within the confines of an autoinjector as a dry powder, for example, the loading of L-epinephrine freebase. In some embodiments the dry drug, for example, L-epinephrine freebase is ground using a mortar and pestle to decrease the particle size and improve the dissolution rate. In some embodiments the L-epinephrine freebase is ground using another means.

In some embodiments, aspects of the invention relate to a method of delivering a drug (e.g., epinephrine) to a subject by dissolving and/or rehydrating and/or mixing a dry composition (e.g., a dry epinephrine) with a solution sufficient to dissolve the dry drug (e.g., to dissolve at least 50%, at least 60%, at least 70%, at least 80%, at least 90%, around 95%, or 90-100% of the dry drug), and delivering the dissolved drug (and, in some embodiments, some quantity of undissolved drug) to a subject via injection (e.g., immediately after dissolving the drug). In some embodiments, this can be accomplished by preloading an autoinjector with a dry drug and a solution to dissolve the dry drug and causing mixing and dissolution of the drug by activating the autoinjector. In some embodiments, the solution to dissolve the dry drug is pH optimized with a buffer. Where pH optimized means a pH that will result in the dissolution of the various forms of epinephrine. In some embodiments the buffer is an acid. In some embodiments the buffer is hydrochloric acid. In some embodiments and epinephrine solution is administered. In some embodiments, an L-epinephrine solution is administered. In some embodiments, an epinephrine salt solution is administered. In some embodiments, the epinephrine salt is a maleate, malate, fumarate, acid tartrate, hydrogen tartrate, or sulfate salt of epinephrine. In some embodiments, the epinephrine salt is epinephrine HCl, epinephrine bitartrate, or epinephrine borate. In some embodiments, the mixing is performed in an autoinjector prior to injection. In some embodiments, the mixing is performed in a prefilled syringe prior to injection. In some embodiments, the subject is a human subject. In some embodiments, the subject is non-human.

In another aspect, the present disclosure provides methods to prepare a medical solution by utilizing the energy released from the ingredients of the solution to dissolve the therapeutic compounds.

In one aspect, provided herein is a method of preparing a medical solution from a dry medicament composition. Such method comprises mixing a first liquid with a second liquid to generate a mixture. In some embodiments, the mixing of the two liquids generates heat to promote solubility of a dry medicament in the mixture. In some embodiments, the first and second liquids are mixed together before contacting the dry medicament composition. However, it should be appreciated that in some embodiments, one of the liquids can be contacted to the dry medicament composition before being mixed with the other liquid, or both liquids and the dry medicament composition can all be mixed together simultaneously as aspects of the disclosure are not limited in this respect.

In another aspect, provided herein is a medical kit comprising a dry medicament, a first liquid, and a second liquid. In some embodiments, heat is produced from mixing the first liquid and the second liquid to promote solubility of the dry medicament in the mixture.

In another aspect, provided herein is a method of preparing a medical solution comprising mixing a solid component with a liquid to generate a solution. The mixing of the solid component and the liquid would generate heat to promote solubility of a dry medicament in the solution.

In another aspect, provided herein is a medical kit comprising a dry medicament and a liquid. Heat would be produced from mixing the dry medicament with the liquid to promote solubility of the dry medicament in the mixture.

DETAILED DESCRIPTION OF FIGURES

FIG. 1 illustrates a method for a single-stage mixing and injection process.

FIGS. 2A-B illustrate a two-step mixing and then injecting the mixed or dissolved solution.

Figure 10:
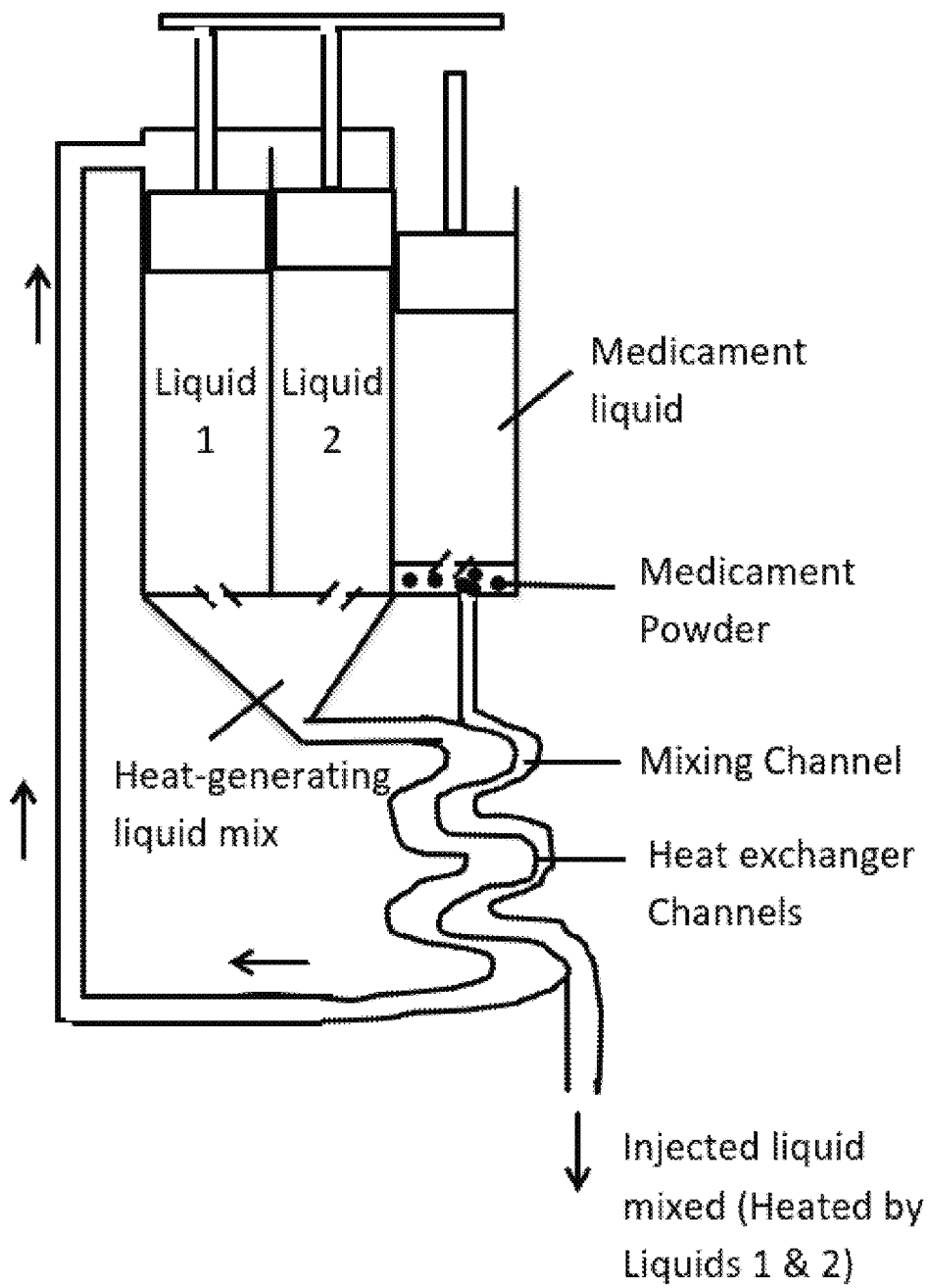

FIG. 10 shows a non-limiting embodiment of an injection device equipped with a microfluidic heat exchanger. Heat may be activated via mixing multiple liquids and/or mixing at least one liquid with at least one solid component through a microfluidic channel. The microfluidic channel is in the form of a closed loop, separate from the mixing channel of the medicament constituents. The exemplified injection device shows heat generated from mixing two liquid reactants. It is understood that the exemplified microfluidic heat exchanger can also be applied to transferring the heat generated from mixing at least one liquid with at least one solid component. A plurality of vials may be added to accommodate more heat-generating components.

Figure 11:
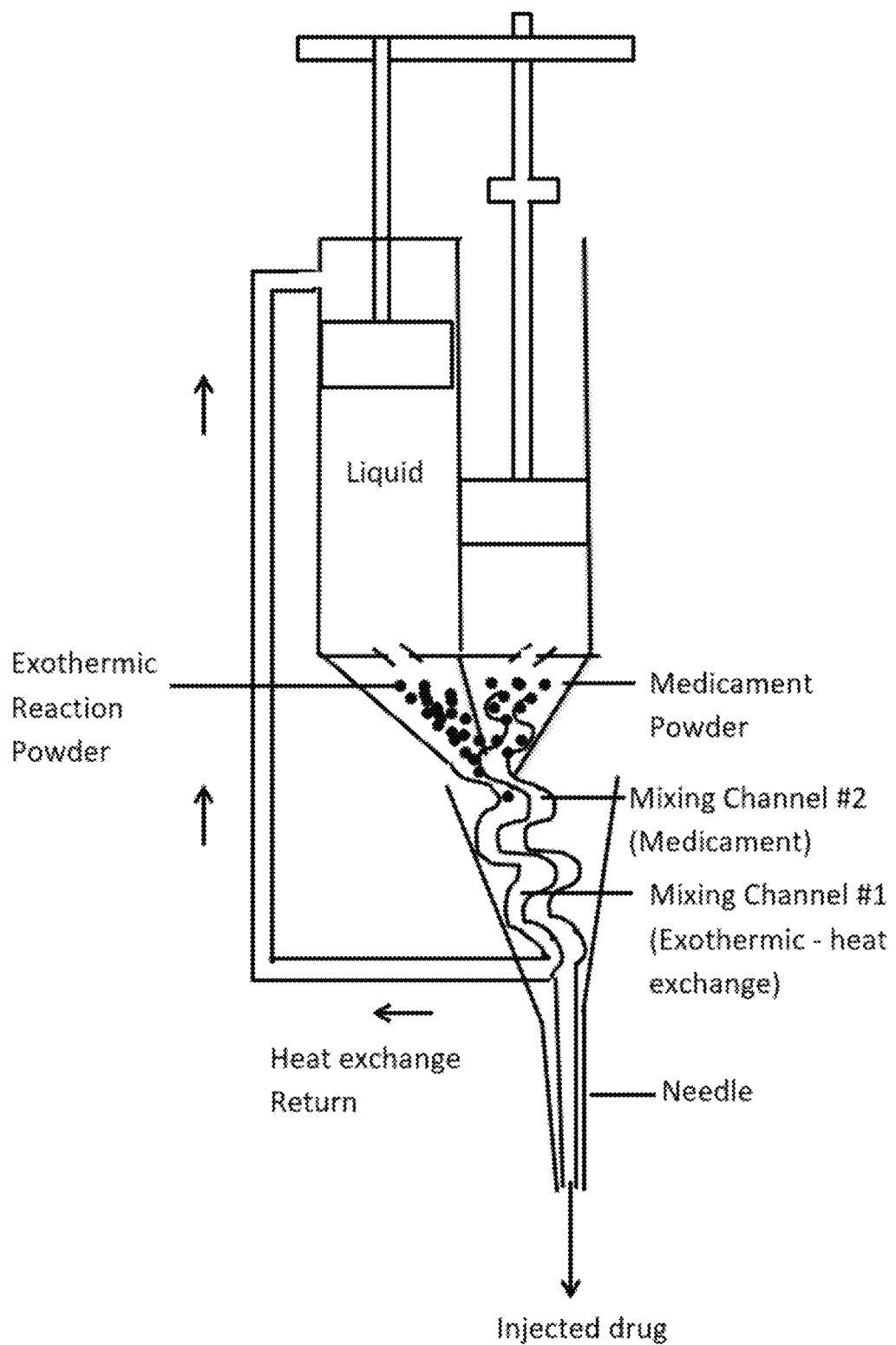

FIG. 11 shows a non-limiting embodiment of an injection device equipped with a microfluidic heat exchanger. Heat may be activated via mixing multiple liquids and/or mixing at least one liquid with at least one solid component through a microfluidic channel. The exemplified injection device shows heat generated from mixing the liquid and the solid component. It is understood that the exemplified microfluidic heat exchanger can also be applied to transferring the heat generated from mixing liquids. A plurality of vials may be added to accommodate more heat-generating components.

DETAILED DESCRIPTION

Provided herein are methods of preparing a medical solution comprising a therapeutic agent. In some embodiments, aspects of the invention relate to stabilizing a drug and making it less susceptible to temperature-induced degradation, by preparing a dry composition (e.g., a dry salt form) of the drug that can be readily reconstituted (e.g., in the context of an autoinjector) for delivery to a patient.

The dry composition can be prepared from any suitable method as used in the pharmaceutical formulation. For example, a drug may be chemically derived, lyophilized (freeze-dried) and/or spray dried and/or using any other technique to put the drug and/or medicament into a dry form. However, in some embodiments, it is important that the dried drug be easily and rapidly soluble so that the dry composition can be used in an autoinjector that also contains a liquid component that can be mixed with the dry drug to solubilize it upon activation of the autoinjector (e.g., immediately prior to or at the time of injection).

There are many common drug formulations that contain epinephrine in some form, including those used to treat cardiac arrest as well as anaphylaxis. Due to the insolubility of epinephrine freebase, finished dosage forms of epinephrine used in healthcare are typically formulated using an acid to form hydrochloride, bitartrate, or borate salts.

Epinephrine freebase is only sparingly soluble in water, while some epinephrine salts dissolve readily. Epinephrine freebase, however, becomes more soluble when properly pH adjusted with an acid, like with hydrochloric acid, to a pH below 6, a pH below 5, a pH between 2-5, a pH between 1-5. Adding metabisulfite to the solution also helps epinephrine freebase dissolve more readily into solution. When used in drug applications, epinephrine is usually administered as a salt dissolved in water, or the equivalent, to form a solution.

In some embodiments, aspects of the invention relate to a dried epinephrine composition. In some embodiments, a composition includes a chemically derived, lyophilized, spray dried, vacuum dried or other method for making a dry composition of matter that includes one or more or all of the following components: epinephrine, an acid or epinephrine along with an acid, sodium chloride or other salt or compound added to adjust tonicity, sodium metabisulfite or other antioxidant and/or manitol. The acid can be of a number of embodiments like hydrochloric acid, sulfuric acid, phosphoric acid, maleic acid and others.

In some embodiments, a dried (e.g., freeze dried) form of (−)-epinephrine Hydrochloride (EpiHCl) is used. It should be appreciated that (−)-epinephrine is also referred to as L-epinephrine. By drying (e.g., freeze-drying) the active ingredient it may be readily soluble in water. Free-base Epinephrine formulated in medical solutions utilizes hydrochloric acid for dissolution, which effectively converts the free base into a soluble salt in solution. The reconstitution of (−)-Epinephrine Hydrochloride as described herein (e.g., in the context of an autoinjector) is therefore equivalent to a formulation of epinephrine base using hydrochloric acid.

In one embodiment, L-epinephrine freebase is placed inside an autoinjector, for example, in one chamber. A solution that is pH optimized with HCl, or any other acid is placed in another chamber. In one embodiment, the HCl solution is of 1M or higher. In some embodiments, the HCl solution is of 0.1M or higher. In some embodiments, the HCl solution is of 0.01M or higher. In some embodiments, the HCl solution is of 0.001M or higher. In some embodiments, the HCl solution is of 0.0001M or higher. In some embodiments, the HCl solution is of 0.00001M or higher. In some embodiments, the HCl solution is of 0.000001M or higher.

Figure 1:
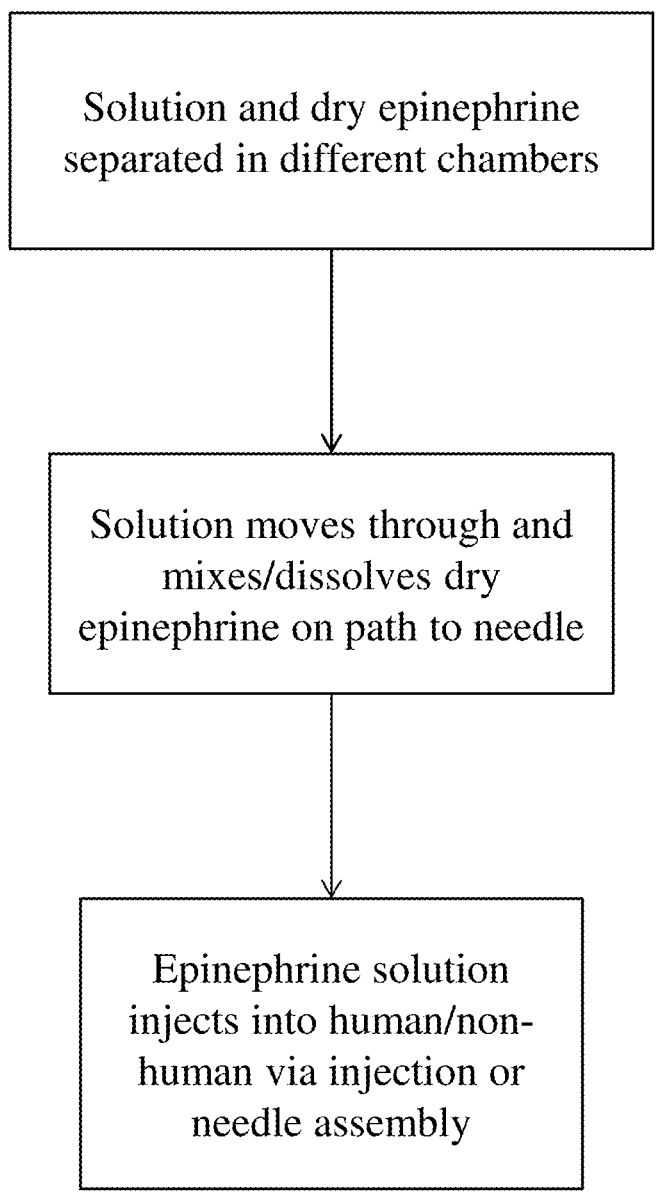

In one embodiment, additional components like metabisulfite, sodium chloride and other materials may also be included in the solution for dissolving the epinephrine. In one embodiment, the autoinjector is activated and/or fluid communication is created between the pH optimized solution and the epinephrine freebase causing the epinephrine freebase to dissolve readily into solution and be injected into the patient, all in one step (FIG. 1).

Figure 2A:
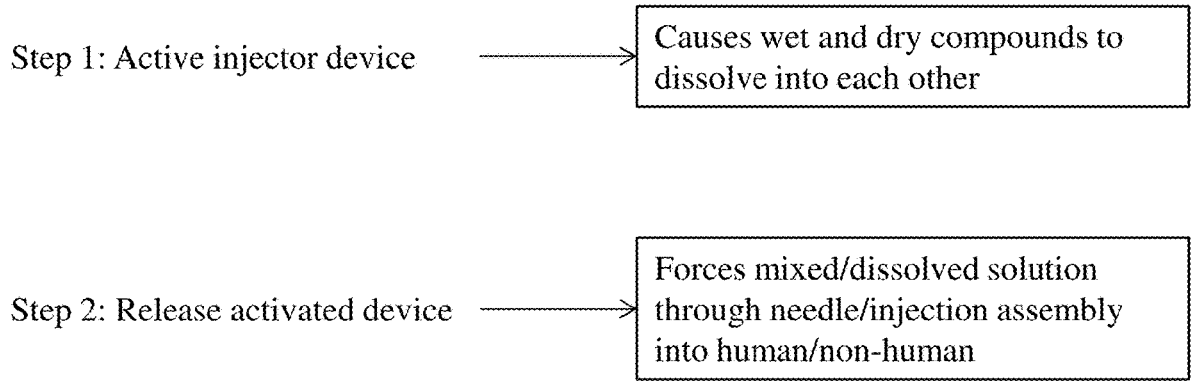
Figure 2B:
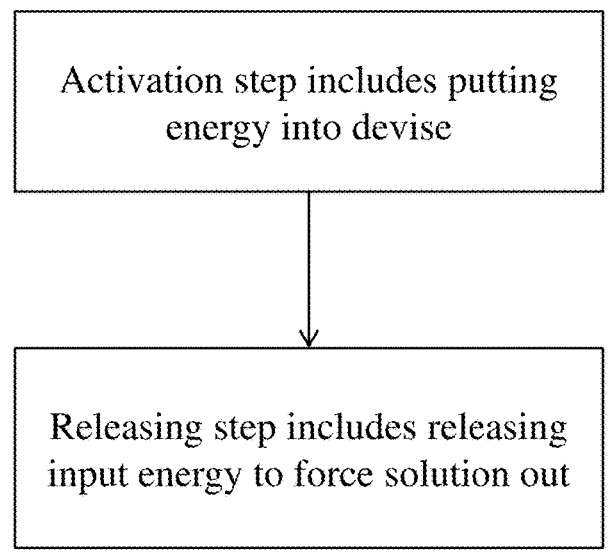
Figure 3:
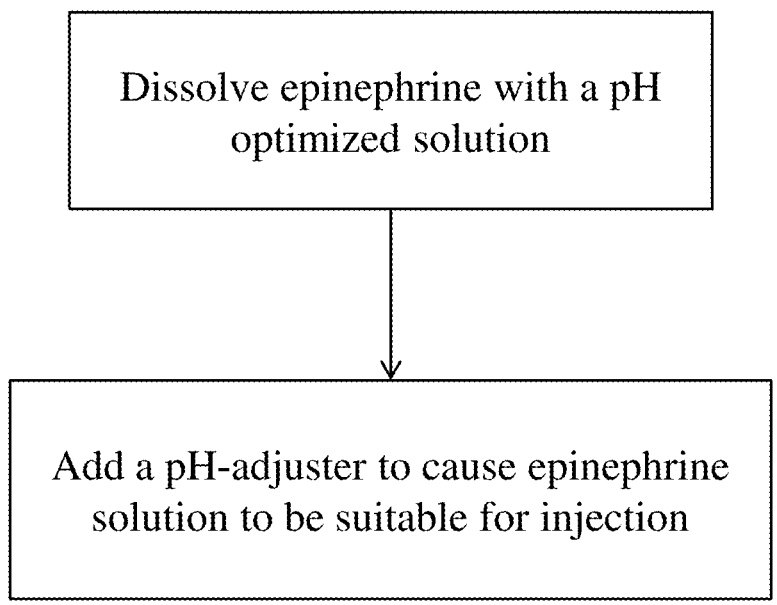
FIG. 3 illustrates a multi-step dissolution method including a fast dissolution step followed by a pH adjusting step causing the solution to be suitable for injecting.

In another embodiment, the dissolving of epinephrine freebase happens in one step and the dissolved solution is held inside the autoinjector or prefilled syringe until a subsequent step and/or input from the user causes the liquid dose of epinephrine to be injected into the body (FIGS. 2A and 2B).

In one embodiment, the epinephrine freebase is dissolved into solution using a first solution (e.g., a pH optimizing solution) so the pH of the dissolved material is below a pH of 6, is below a pH of 5, is below a pH of 4, is below a pH of 3, is below a pH of 2, is between a pH of 2-5. In one embodiments, the dissolved epinephrine solution is secondly adjusted with a second solution (e.g., a pH adjusting solution) so the final pH is physiologically acceptable for administration.

In certain embodiments, the first solution (e.g., the pH optimizing solution) has a pH that is capable of dissolving or solubilizing a medicament dry power (e.g., an epinephrine dry powder). In certain embodiments, the first solution comprises an acid. In certain embodiments, the first solution comprises a base. In certain embodiments, the first solution comprises a buffer.

In certain embodiments, the second solution (e.g., the pH adjusting solution) is capable of adjusting the pH of the medicament solution (e.g., the epinephrine solution), for example to result in a pH that is physiologically acceptable. In certain embodiments, the second solution comprises an acid. In certain embodiments, the second solution comprises a base. In certain embodiments, the second solution comprises a buffer.

In some embodiments, a buffer for adjusting the pH of the dissolved solution is contained inside a reservoir to receive the dissolved solution. For example, this buffer may exist to increase the pH of the dissolved solution above a pH of 2 if a pH upon dissolution drops below a pH of 2. In one embodiment, the pH adjusting solution is water. In one embodiment the pH adjusting solution is a base. In one embodiment, the pH adjusting solution is sodium hydroxide. By adjusting the pH through the pH adjusting buffer, the solution becomes suitable for injection.

In some embodiments, the components of each solution are weighed and measured so that the final concentration of therapeutic agent or medicament (e.g., L-epinephrine) in solution is 1 mg/ml. In one embodiment, the final concentration of therapeutic agent or medicament (e.g., L-epinephrine) is between 0.8 mg/ml and 1.2 mg/ml. In one embodiment, the final concentration of therapeutic agent or medicament (e.g., L-epinephrine) is between 0.7 mg/ml and 1.3 mg/ml. In some embodiments, the final concentration of therapeutic agent or medicament (e.g., L-epinephrine) is less than 0.8 mg/ml, for example less than 0.7 mg/ml. In some embodiments, the final concentration of therapeutic agent or medicament (e.g., L-epinephrine) is greater than 1.2 mg/ml, for example greater than 1.3 mg/ml.

In some embodiments, the concentration of one or more components (e.g., one or more acids, bases, buffers, salts, excipients, therapeutic agents, medicaments, drugs, or other components described herein) ranges from 1 nM to 1 M, for example from 1 nM to 1 µM, from 1 µm to 1 mM, from 1 mM to 10 mM, from 10 mM to 100 mM, from 100 mM to 500 mM, from 500 mM to 1M, about 1 mM, about 5 mM, about 10 mM, about 50 mM, about 100 mM, about 500 mM, about 1M, or higher or lower depending on the component and/or the application.

In some embodiments, aspects of the invention are useful for preparing a dry drug form that a) is stable for extended periods of time and b) can be rapidly dissolved and/or mixed and/or reconstituted into a liquid form for injection. In some embodiments, the dry drug composition is stored in an injector housing along with a liquid that is separated from the dry composition until activation. Activation can bring the liquid and dry phases into contact using any suitable technique or combination of channels, reservoir, seals, and/or electromechanical elements that can be used to control the storage and mixing of the dry and liquid phases.

In some embodiments, aspects of the invention relate to dry epinephrine compositions. Like all medications, drugs or antidotes, epinephrine has a lifetime over which it's acceptably effective, beyond which it has potentially degraded and lost an unacceptable amount of its potency. In addition, degradation of epinephrine can be accelerated when subjected to large temperature fluctuations, especially when the temperature exceeds its acceptable storage temperature. According to aspects of the invention, epinephrine in solution is particularly vulnerable to changes in environmental conditions. For example, in order to maintain potency of an epinephrine solution, a typical epinephrine auto-injector manufacturer recommends that the device be stored at controlled room temperature (20° C.-25° C. with allowable temperature excursions as low as 15° C. and as high as 30° C.). If this temperature range is maintained accurately, the epinephrine can remain stable for up to 20 months from the date of manufacture. Any deviation of the epinephrine and/or auto-injector outside of this recommended temperature range may cause the epinephrine to lose potency resulting in an epinephrine that is less effective and potentially insufficient for reversing the effects of anaphylactic shock. In addition to thermal instability, epinephrine may also degrade when exposed to light, oxygen, and certain materials.

As used herein, a pH optimizing solution refers to a solution that has the capacity to change the pH of a mixture. In certain embodiments, a pH optimizing solution facilitates dissolution of the dry medicament. In certain embodiments, optimizing solution is an acid as generally described herein. In certain embodiments, the optimizing solution is a base as generally described herein. In certain embodiments, the pH optimizing solution is a buffer.

As used herein, a pH adjusting solution is a solution that can alter the pH value of a solution. In certain embodiments, the pH adjusting solution adjusts the pH of the solution physiologically acceptable pH suitable for administration. In certain embodiments, the pH adjusting solution is an acid as generally described herein. In certain embodiments, the pH adjusting solution is a base as generally described herein. In certain embodiments, the pH adjusting solution is a buffer as generally described herein. In certain embodiments, the pH adjusting solution is a salt.

As generally defined herein, an acid is a chemical substance that dissociates in aqueous solution to give $H^+$. In certain embodiments, the acid is an organic acid. In certain embodiments, the acid is an inorganic acid. Examples of the acids include, but are not limited to, 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid, aspartic acid, benzenesulfonic acid, benzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, glucoheptonic acid, gluconic acid, glucuronic acid, glutamic acid, glutaric acid, glycerophosphoric acid, glycolic acid, hippuric acid, hydrobromic acid, hydrochloric acid, isobutyric acid, lactic acid, lactobionic acid, lauric acid, maleic acid, malic acid, malonic acid, mandelic acid, methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, pyroglutamic acid, salicylic acid, sebacic acid, stearic acid, succinic acid, sulfuric acid, tartaric acid, thiocyanic acid, toluenesulfonic acid, or undecylenic acid. In some embodiments, the acid is hydrochloric acid;, sulfuric acid;, phosphoric acid;, maleic acid; 1-hydroxy-2-naphthoic acid; 2,2-dichloroacetic acid; 2-hydroxyethanesulfonic acid; 2-oxoglutaric acid; 4-acetamidobenzoic acid; 4-aminosalicylic acid; acetic acid; adipic acid; ascorbic acid (L); aspartic acid (L); benzenesulfonic acid; benzoic acid; camphoric acid (+); camphor-10-sulfonic acid (+); capric acid (decanoic acid); caproic acid (hexanoic acid); caprylic acid (octanoic acid); carbonic acid; cinnamic acid; citric acid; cyclamic acid; dodecylsulfuric acid; ethane-1,2-disulfonic acid; ethanesulfonic acid; formic acid; fumaric acid; galactaric acid; gentisic acid; glucoheptonic acid (D); gluconic acid (D); glucuronic acid (D); glutamic acid; glutaric acid; glycerophosphoric acid; glycolic acid; hippuric acid; hydrobromic acid; hydrochloric acid; isobutyric acid; lactic acid (DL); lactobionic acid; lauric acid; maleic acid; malic acid (–L); malonic acid; mandelic acid (DL); methanesulfonic acid ; naphthalene-1,5-disulfonic acid; naphthalene-2-sulfonic acid; nicotinic acid; nitric acid; oleic acid; oxalic acid; palmitic acid; pamoic acid; phosphoric acid; proprionic acid; pyroglutamic acid (–L); salicylic acid; sebacic acid; stearic acid; succinic acid; sulfuric acid; tartaric acid (+L); thiocyanic acid; toluenesulfonic acid (p); or undecylenic acid. In some embodiments, the acid is sulfuric acid, hydrochloric acid, hydrobromic acid, nitric acid, phosphoric acid, perchloric acid, formic acid, acetic acid, propionic acid, oxalic acid, maleic acid, citric acid, succinic acid, malonic acid, tartaric acid, or combinations thereof. In certain embodiments, the acid is hydrochloric acid, nitric acid, sulfuric acid, phosphoric acid, tartaric acid, malic acid, malonic acid, maleic acid, fumaric acid, succinic acid, or formic acid.

As generally defined herein, a base is a chemical substance that dissociates in aqueous solution to give $OH^-$. In certain embodiments, the base is an organic base. In certain embodiments, the base is an inorganic base. In certain embodiments, the base is an alkaline base. Examples of the bases include, but are not limited to, sodium citrate, sodium acetate, sodium hydroxide, potassium hydroxide, lithium hydroxide, ammonium hydroxide, calcium hydroxide, magnesium hydroxide, iron hydroxide, zinc hydroxide, copper hydroxide, manganese hydroxide, aluminum hydroxide, isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, tromethamine, N-methylglucamine, or combinations thereof. In some embodiments, the base is sodium hydroxide or potassium hydroxide.

As used herein, the term "buffer" refers to either a buffering agent or a buffering solution comprising one or more buffering agents. As generally defined herein, a buffering agent is a weak acid or base used to maintain the pH of a solution near a chosen value after the addition of another acid or base. The function of a buffering agent is to prevent a rapid change in pH when acids or bases are added to the solution. Exemplary buffering agents include but are not limited to citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof. In certain embodiments, the buffer is a sodium salt, a calcium salt, a potassium salt, or an ammonium salt. In certain embodiments, the buffer is a citrate, acetate, phosphate, sulfate, nitrate, tartrate, succinate, malate, or maleate. In certain embodiments, the buffer is sodium citrate, sodium acetate, potassium hydroxide, potassium citrate, potassium acetate, sodium succinate, or potassium succinate.

As used herein, the first liquid can be a solvent or a solution. In some embodiments, the first liquid is a single solvent. In some embodiments, the first liquid is a solution comprising a pH optimizing agent and a single solvent. In some embodiments, the first liquid comprises water. In some embodiments, the first liquid comprises water and a pH optimizing agent. In some embodiments, the pH optimizing agent is an acid as generally defined herein. In some embodiments, the pH optimizing agent is HCl. In some embodiments, the first liquid is an aqueous solution comprising HCl. In some embodiments, the pH optimizing agent is a base as generally defined herein. In some embodiments, the pH optimizing agent is an alkaline base.

In some embodiments, the pH of the first liquid is from about 0.1 to about 6.9. In some embodiments, the pH of the first liquid is from about 0.5 to about 5.0. In some embodiments, the pH of the first liquid is from about 1.0 to about 5.0. In some embodiments, the pH of the first liquid is from about 2.0 to about 5.0. In one embodiment, the pH of the first liquid is from about 0.1 to about 6.0. In one embodiment, the pH of the first liquid is from about 0.1 to about 5.0. In one embodiment, the pH of the first liquid is from about 0.1 to about 4.0. In one embodiment, the pH of the first liquid is from about 0.1 to about 3.0. In one embodiment, the pH of the first liquid is from about 0.1 to about 2.0. In one embodiment, the pH of the first liquid is from about 0.1 to about 1.0. In one embodiment, the pH of the first liquid is from about 0.01 to about 2.2 and the dry medicament is epinephrine.

In some embodiments, the pH of the first liquid is from about 7.0 to about 13.5. In some embodiments, the pH of the first liquid is from about 8.0 to about 13.5. In some embodiments, the pH of the first liquid is from about 9.0 to about 13.5. In some embodiments, the pH of the first liquid is from about 9.5 to about 13.5. In some embodiments, the pH of the first liquid is from about 9.5 to about 13.5 and the dry medicament is glucagon.

The disclosure further provides compositions of a medical solution and methods for preparing a medical solution from a therapeutic agent in a solid form over a short period of time (e.g., a few minutes to a few seconds). Aspects of the disclosure relate to generating energy (e.g., in the form of a change in temperature) from mixing two or more ingredients of a medical preparation and using that energy to help to prepare a solution of a medicament that is suitable for administration to a subject.

Methods provided herein are advantageous in situations where a drug in solid form does not dissolve readily upon contact with a liquid. In such situations, typical preparative methods involve additional time and energy (e.g., vigorous shaking over many minutes) to dissolve and/or reconstitute a drug prior to administration. This shaking may be detrimental in cases where immediate drug delivery is required in an emergency setting. In other cases, it may be difficult to produce a solution suitable for administration within a prefilled syringe or an auto-injector, e.g., where this type of reconstitution of a solid drug may produce a foam or other form unsuitable for injection, or in cases where the drug degrades during reconstitution. The present disclosure overcomes disadvantages of shaking by utilizing energy (e.g., heat) generated from mixing two or more ingredients (e.g., one liquid component with another liquid component or solid component) of a medical solution. The energy (e.g., heat) can be reabsorbed to promote the dissolution of a dry medicament. The medical solutions prepared from the methods described herein can be administered in any route or by any device, for example, a prefilled syringe or an autoinjector device (e.g., an EpiPen).

In one aspect, the invention provides a method of preparing a medical solution from a dry medicament, comprising mixing a first liquid with a second liquid to generate a mixture. The mixing of the two liquids generates heat to promote solubility of the dry medicament in the mixture. In certain embodiments, the invention provides a method of preparing a medical solution from a dry medicament, comprising mixing a first liquid, a second liquid, and at least another liquid to generate a mixture. The mixing of at least two liquids generates heat to promote solubility of the dry medicament in the mixture.

In some embodiments, the heat is released from an exothermic chemical reaction from mixing the first liquid and the second liquid. As used herein, an exothermic reaction is a chemical reaction that releases energy in the form of light or heat. In some embodiments, the heat is released in the range of about 0 kcal to 5000 kcal per mol of the therapeutic agent. In some embodiments, the heat is released in the range of about 0 kcal to 3000 kcal per mol of the therapeutic agent. In some embodiments, the heat is released in the range of about 0 kcal to 1000 kcal per mol of the therapeutic agent. In some embodiments, the heat is released in the range of about 0 kcal to 500 kcal per mol of the therapeutic agent. In some embodiments, the heat is released in the range of about 0 kcal to 300 kcal per mol of the therapeutic agent. In some embodiments, the heat is released in the range of about 0 kcal to 100 kcal per mol of the therapeutic agent. In some embodiments, the heat is released in the range of about 0 kcal to 50 kcal per mol of the therapeutic agent. In some embodiments, the heat is released in the range of about 0 kcal to 30 kcal per mol of the therapeutic agent. In some embodiments, the heat is released in the range of about 0 kcal to 20 kcal per mol of the therapeutic agent. In some embodiments, the heat is released in the range of about 0 kcal to 10 kcal per mol of the therapeutic agent. In some embodiments, the released heat is at least about 1 kcal per mol of the therapeutic agent. In some embodiments, the released heat is at least about 5 kcal per mol of the therapeutic agent. In some embodiments, the released heat is at least about 10 kcal per mol of the therapeutic agent. In some embodiments, the released heat is at least about 20 kcal per mol of the therapeutic agent. In some embodiments, the released heat is at least about 30 kcal per mol of the therapeutic agent. In some embodiments, the released heat is at least about 40 kcal per mol of the therapeutic agent. In some embodiments, the released heat is at least about 50 kcal per mol of the therapeutic agent. In some embodiments, the released heat is at least about 1 kcal per mol of the therapeutic agent and at most about 100 kcal per mol of the therapeutic agent. In some embodiments, the released heat is at least about 5 kcal per mol of the therapeutic agent and at most about 100 kcal per mol of the therapeutic agent. In some embodiments, the released heat is at least about 10 kcal per mol of the therapeutic agent and at most about 100 kcal per mol of the therapeutic agent. In some embodiments, the released heat is at least about 20 kcal per mol of the therapeutic agent and at most about 100 kcal per mol of the therapeutic agent. In some embodiments, the released heat is at least about 30 kcal per mol of the therapeutic agent and at most about 100 kcal per mol of the therapeutic agent. In some embodiments, the released heat is at least about 40 kcal per mol of the therapeutic agent and at most about 100 kcal per mol of the therapeutic agent. In some embodiments, the released heat is at least about 50 kcal per mol of the therapeutic agent and at most about 100 kcal per mol of the therapeutic agent. It should be appreciated that the amount of energy released per mol of the therapeutic agent can be determined by providing an appropriate ratio of heat generating reagents (e.g., first and second solutions or a liquid and a solid component) to the therapeutic agent. The heat or energy is released from mixing of the heat generating reagents (e.g., first and second solutions or a liquid and a solid component) as described herein. In some embodiments, the heat is reabsorbed in dissolution of the dry medicament in the mixture.

In some embodiments, the dry medicament is subsequently added to the mixture formed by the first liquid and the second liquid. In some embodiments, the dry medicament is added to the first liquid before the first liquid is mixed with the second liquid.

As used herein, the dry medicament can be of any solid form. In some embodiments, the dry medicament is a powder. In some embodiments, the powdered form of the dry medicament is prepared from lyophilizing a liquid medication. In some embodiments, the powdered form of the dry medicament is prepared from spray-drying, vacuum drying, or chemically precipitating out of a medical solution. In some embodiments this dry medicament is amorphous. In another embodiment this dry medicament is crystalline. In some embodiments the dry medicament can form a porous matrix. In some embodiments the dry medicament can form a loose assemblage of powder. In some embodiments the dry medicament can form a loose assemblage of porous matrix. In some embodiments the dry medicament can form a loose assemblage of powder with particles (e.g., in the size of about 1 nm to about 1000 µm). In some embodiments, the dry medicament can form a loose assemblage of powder with the particle size ranging from about 1 nm to about 500 µm. In some embodiments, the dry medicament can form a loose assemblage of powder with the particle size ranging from about 1 nm to about 100 µm. In some embodiments, the dry medicament can form a loose assemblage of powder with the particle size ranging from about 1 nm to about 50 p.m. In some embodiments, the dry medicament can form a loose assemblage of powder with the particle size ranging from about 1 nm to about 10 µm. In some embodiments, the dry medicament can form a loose assemblage of powder with the particle size ranging from about 1 nm to about 1 µm. In some embodiments, the dry medicament can form a loose assemblage of powder with the particle size ranging from about 1 nm to about 500 nm. In some embodiments, the dry medicament can form a cake consisting of a porous matrix with particles (e.g., in the size of about 1 nm to about 1000 µm). In some embodiments, the dry medicament can form a cake consisting of a porous matrix with the particle size ranging from about 1 nm to about 500 µm. In some embodiments, the dry medicament can form a cake consisting of a porous matrix with the particle size ranging from about 1 nm to about 100 µm. In some embodiments, the dry medicament can form a cake consisting of a porous matrix with the particle size ranging from about 1 nm to about 50 µm. In some embodiments, the dry medicament can form a cake consisting of a porous matrix with the particle size ranging from about 1 nm to about 10 µm. In some embodiments, the dry medicament can form a cake consisting of a porous matrix with the particle size ranging from about 1 nm to about 1 µm. In some embodiments, the dry medicament can form a cake consisting of a porous matrix with the particle size ranging from about 1 nm to about 500 nm. In some embodiments, the dry medicament can form a cake consisting of a porous matrix with the particle size ranging from about 1 nm to about 100 nm.

In some embodiments, the dry medicament comprises one therapeutic agent. In some embodiments, the dry medicament comprises two or more therapeutic agents. In some embodiments, the dry medicament comprises one therapeutic agent and a pharmaceutically acceptable excipient. In some embodiments, the dry medicament comprises two or more therapeutic agents and a pharmaceutically acceptable excipient.

As used herein, a therapeutic agent refers to a substance used for the treatment, prevention, cure or mitigation of disease or illness, by affecting the structure or function of the body. The therapeutic agents include pro-drugs, which become biologically active or more active after they have been placed in a predetermined physiological environment. Examples of therapeutic agents include, but are not limited to, small-molecule drugs, peptides, proteins, antibodies, sugars, polysaccharides, nucleotides, oligonucleotides, aptamers, siRNA, nucleic acids, and combinations thereof.

In some embodiments, the therapeutic agent is an anti-inflammatory agent, an antimicrobial agent, an antifungal agent, an anti-parasitic agent, an anti-inflammatory agent, an anti-cancer agent, an agent for treatment of a cardiovascular disease, an agent for treatment of an allergy reaction, or a pain-relieving agent. In some embodiments, the therapeutic agent is an agent for treatment of an allergy reaction. In some embodiments, the agent is for treatment of anaphylaxis. In some embodiments, the agent is epinephrine.

Exemplified therapeutic agents include, but are not limited to, anti-inflammatory, antipyretic, anti-spasmodics or analgesics such as indomethacin, diclofenac, diclofenac sodium, codeine, ibuprofen, phenylbutazone, oxyphenbutazone, mepirizole, aspirin, ethenzamide, acetaminophen, aminopyrine, phenacetin, butylscopolamine bromide, morphine, etomidoline, pentazocine, fenoprofen calcium, naproxen, selecxip, valdecxip, and tolamadol, anti-rheumatism drugs such as etodolac, anti-tuberculoses drugs such as isoniazide and ethambutol hydrochloride, cardiovascular drugs such as isosorbide dinitrate, nitroglycerin, nifedipine, barnidipine hydrochloride, nicardipine hydrochloride, dipyridamole, amrinone, indenolol hydrochloride, hydralazine hydrochloride, methyldopa, furosemide, spironolactone, guanethidine nitrate, reserpine, amosulalol hydrochloride, lisinopril, metoprolol, pilocarpine, and talcetin, antipsychotic drugs such as chlorpromazine hydrochloride, amitriptyline hydrochloride, nemonapride, haloperidol, moperone hydrochloride, perphenazine, diazepam, lorazepam, chlorodiazepoxide, adinazolam, alprazolam, methylphenidate, myrnasipran, peroxetin, risperidone, and sodium valproate, anti-emetics such as metoclopramide, lamocetron hydrochloride, granisetron hydrochloride, ondansetron hydrochloride, and azacetron hydrochloride, antihistamines such as chlorpheniramine maleate and diphenhydramine hydrochloride, vitamins such as thiamine nitrate, tocopherol acetate, cycothiamine, pyridoxal phosphate, cobarnamide, ascortic acid, and nicotinamide, antigout drugs such as allopurinol, colchicine, and probenecide, anti-Parkinson's disease drugs such as levodopa and selegrine, sedatives and hypnotics such as amobarbital, bromuralyl urea, midazolam, and chloral hydrate, antineoplastics such as fluorouracil, carmofur, acralvidine hydrochloride, cyclophosphamide, and thiodepa, anti-allergy drugs such as pseudoephedrine and terfenadine, decongestants such as phenylpropanolamine and ephedorine, diabetes mellitus drugs such as acetohexamide, insulin, tolbutamide, desmopressin, and glipizide, diuretics such as hydrochlorothiazide, polythiazide, and triamterene, bronchodilators such as aminophylline, formoterol fumarate, and theophylline, antitussives such as codeine phosphate, noscapine, dimorfan phosphate, and dextromethorphan, anti-arrhythmics such as quinidine nitrate, digitoxin, propafenone hydrochloride, and procainamide, topical anesthetics such as ethyl aminobenzoate, lidocaine, and dibucaine hydrochloride, anti-convulsants such as phenyloin, ethosuximide, and primidone, synthetic glucocorticoids such as hydrocortisone, prednisolone, triamcinolone, and betamethasone, antiulceratives such as famotidine, ranitidine hydrochloride, cimetidine, sucralfate, sulpiride, teprenone, plaunotol, 5-aminosalicylic acid, sulfasalazine, omeprazole, and lansoprazol, central nervous system drugs such as indeloxazine, idebenone, thiapride hydrochloride, bifemelane hydrocide, and calcium homopantothenate, antihyperlipoproteinemics such as pravastatin sodium, simvastatin, lovastatin, and atorvastatin, antibiotics such as ampicillin hydrochloride, phthalylsulfacetamide, cefotetan, and josamycin, BPH therapeutic agents such as tamsulosin hydrochloride, doxazosin mesylate, and terazosin hydrochloride, drugs affecting uterine motility such as branylcast, zafylcast, albuterol, ambroxol, budesonide, and reproterol, peripheral circulation improvers of prostaglandin I derivatives such as beraprost sodium, anticoagulants, hypotensives, agents for treatment of cardiac insufficiency, agents used to treat the various complications of diabetes, peptic ulcer therapeutic agents, skin ulcer therapeutic agents, agents used to treat hyperlipemia, tocolytics, etc.

In certain embodiments, the therapeutic agent is selected from the group consisting of Agrylin (anagrelide HCl), Akten (lidocaine hydrochloride), Apokyn (apomorphine hydrochloride), Arestin (minocycline hydrochloride), Avandamet (rosiglitazone maleate and metformin HCl), Avelox I.V. (moxifloxacin hydrochloride), Cardizem (R) (Diltiazem HCl for injection), Contrave (naltrexone HCl and bupropion HCl), Gemzar (gemcitabine HCL), Hycamtin (topotecan hydrochloride), Lamisil (terbinafine hydrochloride), Metozolv ODT (metoclopramide hydrochloride), Namenda (memantine HCl), Paxil (paroxetine hydrochloride), Oxecta (oxycodone HCl), Quillivant XR (methylphenidate hydrochloride), Redux (dexfenfluramine hydrochloride), Relpax (eletriptan hydrobromide), Reminyl (galantamine hydrobromide), Renagel (sevelamer hydrochloride), Requip (ropinirole hydrochloride), Ritalin LA (methylphenidate HCl), Savella (milnacipran hydrochloride), Strattera (atomoxetine HCl), Tasigna (nilotinib hydrochloride monohydrate), Tiazac (diltiazem hydrochloride), Valcyte (valganciclovir HCl), Valtrex (valacyclovir HCl), VERSED (midazolam HCl), Zanaflex (tizanidine hydrochloride), Zingo (lidocaine hydrochloride monohydrate), Ziprasidone (ziprasidone hydrochloride), Zoloft (sertraline HCl), Zometa (zoledronic acid), Zyrtec (cetirizine HCl), glucagon, or sumatriptan.

Pharmaceutically acceptable excipients include any and all diluents, dispersions, suspension aids, surface active agents, isotonic agents, thickening or emulsifying agents, preservatives, solid binders, lubricants, and the like, as suited to the particular dosage form desired. General considerations in formulation and/or manufacture of pharmaceutical compositions agents can be found, for example, in *Remington's Pharmaceutical Sciences*, Sixteenth Edition, E. W. Martin (Mack Publishing Co., Easton, Pa., 1980), and *Remington: The Science and Practice of Pharmacy*, 21st Edition (Lippincott Williams & Wilkins, 2005).

As used herein, the first liquid can be a solvent or a solution. In some embodiments, the first liquid is a single solvent. In some embodiments, the first liquid is a solution comprising a solute and a single solvent. In some embodiments, the first liquid is a solution comprising two or more solvents. In some embodiments, the first liquid comprises a solvent and a cosolvent. In some embodiments, the first liquid comprises water. In some embodiments, the first liquid is water. In some embodiments, the first liquid is an aqueous solution. In some embodiments, the first liquid comprises a non-aqueous solvent, for example, a polar solvent (e.g., dimethyl sulfoxide, ethyl acetate, n-butanol, ethanol, isopropanol, or n-propanol), or a non-polar solvent (e.g., alkane hydrocarbons such as hexane). In some embodiments, the first liquid comprises water and a cosolvent. Examples of cosolvent that can be used with water are PEG 300, propylene glyco or ethanol.

In some embodiments, the first liquid can further comprise a non-therapeutic agent. In some embodiments, the first liquid is an aqueous solution comprising a non-therapeutic agent. The non-therapeutic agent acts to modify the solubility of at least one therapeutic agent. In some embodiments, the non-therapeutic agent is an acid. In some embodiments, the non-therapeutic agent is a pharmaceutically acceptable acid. In some embodiments, the non-therapeutic agent is a pharmaceutically acceptable organic acid. In some embodiments, the non-therapeutic agent is a pharmaceutically acceptable inorganic acid. Examples of the acids for the non-therapeutic agents include, but are not limited to, 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid, aspartic acid, benzenesulfonic acid, benzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, glucoheptonic acid, gluconic acid, glucuronic acid, glutamic acid, glutaric acid, glycerophosphoric acid, glycolic acid, hippuric acid, hydrobromic acid, hydrochloric acid, isobutyric acid, lactic acid, lactobionic acid, lauric acid, maleic acid, malic acid, malonic acid, mandelic acid, methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, pyroglutamic acid, salicylic acid, sebacic acid, stearic acid, succinic acid, sulfuric acid, tartaric acid, thiocyanic acid, toluenesulfonic acid, or undecylenic acid. In some embodiments, the acid is sulfuric acid, hydrochloric acid, hydrobromic acid, nitric acid, phosphoric acid, perchloric acid, formic acid, acetic acid, propionic acid, oxalic acid, maleic acid, citric acid, succinic acid, malonic acid, tartaric acid, or combinations thereof.

In some embodiments, the pH of the first liquid is less than about 0.1. In some embodiments, the pH of the first liquid is from about 0.1 to about 6.9. In some embodiments, the pH of the first liquid is from about 0.5 to about 5.0. In some embodiments, the pH of the first liquid is from about 1.0 to about 5.0. In some embodiments, the pH of the first liquid is from about 2.0 to about 5.0. In some embodiments, the pH of the first liquid is from about 2.0 to about 4.0.

As used herein, the second liquid can be a solvent or a solution. In some embodiments, the second liquid is a single solvent. In some embodiments, the second liquid is a solution comprising a solute and a single solvent. In some embodiments, the second liquid is a solution comprising two or more solvents. In some embodiments, the second liquid comprises a solvent and a cosolvent. In some embodiments, the second liquid comprises water. In some embodiments, the second liquid is water. In some embodiments, the second liquid is an aqueous solution. In some embodiments, the second liquid comprises a non-aqueous solvent, for example, a polar solvent (e.g., dimethyl sulfoxide, ethyl acetate, n-butanol, ethanol, isopropanol, or n-propanol), or a non-polar solvent (e.g., alkane hydrocarbons such as hexane). In some embodiments, the second liquid comprises water and a cosolvent. Examples of cosolvent that can be used with water are PEG 300, propylene glycol or ethanol.

In some embodiments, the second liquid further comprises a non-therapeutic agent. In some embodiments, the second liquid is an aqueous solution comprising a non-therapeutic agent. In some embodiments, the non-therapeutic agent in the second liquid acts to modify the pH of the first liquid upon mixing. In some embodiments, the non-therapeutic agent in the second liquid is a base. In some embodiments, the non-therapeutic agent in the second liquid is a pharmaceutically acceptable base. In some embodiments, the non-therapeutic agent is a pharmaceutically acceptable organic base. In some embodiments, the non-therapeutic agent is a pharmaceutically acceptable inorganic base. In some embodiments, the base is an alkaline base. Examples of the base that can be used in the second liquid include, but are not limited to, sodium hydroxide, potassium hydroxide, lithium hydroxide, ammonium hydroxide, calcium hydroxide, magnesium hydroxide, iron hydroxide, zinc hydroxide, copper hydroxide, manganese hydroxide, aluminum hydroxide, isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, tromethamine, N-methylglucamine, or combinations thereof. In some embodiments, the base is LiOH, KOH, or NaOH.

In some embodiments, the pH of the second liquid is from about 7.0 to about 14.0. In some embodiments, the pH of the second liquid is from about 7.0 to about 12.0. In some embodiments, the pH of the second liquid is from about 7.0 to about 10.0. In some embodiments, the pH of the second liquid is from about 8.0 to about 10.0.

In some embodiments, the first liquid is an aqueous solution comprising hydrochloric acid and the second liquid is an aqueous solution comprising NaOH. In some embodiments, the first liquid is an aqueous solution comprising hydrochloric acid and a dry medicament, and the second liquid is an aqueous solution comprising NaOH.

Upon medication administration, the dry medicament is often dissolved and/or rehydrated into its liquid form before delivering to a human or non-human patient. In some embodiments, the dry medicament is subsequently added to the mixture formed by the first liquid and the second liquid. In some embodiments, the dry medicament is added to the first liquid prior to mixing with the second liquid. In some embodiments, the dry medicament is added to the second liquid prior to mixing with the first liquid. In some embodiments, the first liquid is a solution comprising a dry medicament. In some embodiments, the first liquid is an aqueous solution comprising the dry medicament. In some embodiments, the first liquid is an aqueous solution comprising a dry medicament and an acid (e.g., sulfuric acid, hydrochloric acid, hydrobromic acid, sulfuric acid, nitric acid, phosphoric acid, perchloric acid, formic acid, acetic acid, propionic acid, oxalic acid, maleic acid, citric acid, succinic acid or malonic acid, tartaric acid, or combinations thereof). In some embodiments, the first liquid is a solution comprising a dry medicament, a solvent and a cosolvent. In some embodiments, the first liquid is a solution comprising a dry medicament, a non-therapeutic agent, a solvent and a cosolvent.

The present invention overcomes the disadvantages of shaking by utilizing the heat generated from mixing some ingredients of the medical solution. In some embodiments, heat is released from mixing the first liquid and the second liquid. In some embodiments, heat is released from the exothermic reaction between the first liquid and the second liquid. The exothermic reaction may be capable of causing a change in the temperature of the solution(s). In some embodiments, the exothermic reaction raises the temperature of the solution(s) by about 1° C., by about about 1° C. to about 2° C., by about 2° C., by about 2° C. to about 3° C., by about 3° C., by about 3° C. to about 4° C., by about 4° C., by about 4° C. to about 5° C., by about 5° C., by about 5° C. to about 10° C., about 10° C., by about 10° C., or above 10° C. relative to the temperature of the solution(s) prior to mixing.

In some embodiments, heat is released from a first liquid comprising an acid with a second liquid comprising a base. In some embodiments, heat is released from mixing a first liquid comprising a strong acid with a second liquid comprising a strong base. In some embodiments, heat is released from mixing a first liquid comprising a strong acid with a second liquid comprising a weak base. In some embodiments, heat is released from mixing a first liquid comprising a weak acid with a second liquid comprising a strong base. In some embodiments, this would be accomplished by mixing a first liquid comprising a weak acid with a second liquid comprising a weak base. In some embodiments, this would be accomplished by mixing a first liquid comprising an acid with a second liquid comprising a buffer. In some embodiments, this would be accomplished by mixing a first liquid comprising a buffer with a second liquid comprising a base.

In some embodiments, the provided method mixes a first liquid comprising an aqueous HCl solution with a second liquid comprising an aqueous NaOH solution to promote solubility of epinephrine freebase. Epinephrine freebase is not particularly soluble in water. The solubility of epinephrine increases in an acidic environment. In some embodiments, epinephrine freebase is dissolved in an aqueous solution comprising HCl. Epinephrine freebase can be protonated and fully dissolved upon adjustment of the pH value of the solution.

In some embodiments, addition of a second liquid comprising NaOH to the first liquid comprising epinephrine and HCl can further increase the solubility of epinephrine. In certain embodiments, addition of a second liquid comprising NaOH to the first liquid comprising epinephrine and HCl can further increase the solubility of epinephrine by increasing the temperature and thus increase the solubility of the epinephrine at a higher pH than would normally be achievable by adding HCl alone.

Relative amounts of the therapeutic agent and/or the pharmaceutically acceptable excipient will vary, depending upon the identity, size, and/or condition of the subject treated and further depending upon the route by which the medical solution is to be administered. By way of example, the medical solution may comprise between 0.1% and 100% (w/w) one or more therapeutic agents.

The medical solution provided herein may comprises a buffering agent. In some embodiments, the buffering agent is in the first liquid. In some embodiments, the buffering agent is in the second liquid. In some embodiment, the buffering agent is added after the first liquid is mixed with the second liquid. Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

The provided medical solution can be delivered by intradermal, intramuscular, intranasal, intravenous, oral, rectal, subcutaneous, topical, or vaginal administration. In certain embodiments, the provided medical solution is administered intradermally or intramuscularly. Suitable devices for use in delivering intradermal or intramuscular medical solution described herein include conventional syringes or short needle devices such as those described in U.S. Pat. No. 4,886,499; 5,190,521; 5,328,483; 5,527,288; 4,270,537; 5,015,235; 5,141,496; and 5,417,662.

In some embodiments, the amount of a therapeutic agent in the medical solution is an effective amount sufficient to elicit the desired biological response, i.e., treat the condition. In some embodiment, the amount of a therapeutic agent in the medical solution is a therapeutically effective amount sufficient to provide a therapeutic benefit in the treatment of a condition or to delay or minimize one or more symptoms associated with the condition. The term "therapeutically effective amount" can encompass an amount that improves overall therapy, reduces or avoids symptoms or causes of the condition, or enhances the therapeutic efficacy of another therapeutic agent. In some embodiments, the effective amount is prophylactically effective amount sufficient to prevent a condition, or one or more symptoms associated with the condition or prevent its recurrence.

As used herein, the effective amount of a therapeutic agent will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the compounds of the invention may be at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

In certain embodiments, provided herein is a medical kit comprising a dry medicament, a first liquid, and a second liquid, wherein mixing the first liquid and the second liquid produces heat to promote solubility of the dry medicament in the mixture. In some embodiments, provided kit may optionally further include a second container comprising a pharmaceutical excipient for dilution or suspension of the therapeutic agent. In some embodiments, the first liquid, the second liquid, and the dry medicament are combined to form one unit dosage form.

The invention provides a method of preparing a medical solution from a dry medicament, comprising mixing a solid component with a liquid to generate a solution. The mixing of the solid component with a liquid generates heat to promote solubility of a dry medicament in the solution.

In some embodiments, the heat is released from an exothermic chemical reaction from mixing the solid component with the liquid. In some embodiments, the heat is released in the range of about 0 kcal to 5000 kcal per mol of the therapeutic agent. In some embodiments, the heat is released in the range of about 0 kcal to 3000 kcal per mol of the therapeutic agent. In some embodiments, the heat is released in the range of about 0 kcal to 1000 kcal per mol of the therapeutic agent. In some embodiments, the heat is released in the range of about 0 kcal to 500 kcal per mol of the therapeutic agent. In some embodiments, the heat is released in the range of about 0 kcal to 300 kcal per mol of the therapeutic agent. In some embodiments, the heat is released in the range of about 0 kcal to 100 kcal per mol of the therapeutic agent. In some embodiments, the heat is released in the range of about 0 kcal to 50 kcal per mol of the therapeutic agent. In some embodiments, the heat is released in the range of about 0 kcal to 30 kcal per mol of the therapeutic agent. In some embodiments, the heat is released in the range of about 0 kcal to 20 kcal per mol of the therapeutic agent. In some embodiments, the heat is released in the range of about 0 kcal to 10 kcal per mol of the therapeutic agent. In some embodiments, the released heat is at least about 1 kcal per mol of the therapeutic agent. In some embodiments, the released heat is at least about 5 kcal per mol of the therapeutic agent. In some embodiments, the released heat is at least about 10 kcal per mol of the therapeutic agent. In some embodiments, the released heat is at least about 20 kcal per mol of the therapeutic agent. In some embodiments, the released heat is at least about 30 kcal per mol of the therapeutic agent. In some embodiments, the released heat is at least about 40 kcal per mol of the therapeutic agent. In some embodiments, the released heat is at least about 50 kcal per mol of the therapeutic agent. In some embodiments, the released heat is at least about 1 kcal per mol of the therapeutic agent and at most about 100 kcal per mol of the therapeutic agent. In some embodiments, the released heat is at least about 5 kcal per mol of the therapeutic agent and at most about 100 kcal per mol of the therapeutic agent. In some embodiments, the released heat is at least about 10 kcal per mol of the therapeutic agent and at most about 100 kcal per mol of the therapeutic agent. In some embodiments, the released heat is at least about 20 kcal per mol of the therapeutic agent and at most about 100 kcal per mol of the therapeutic agent. In some embodiments, the released heat is at least about 30 kcal per mol of the therapeutic agent and at most about 100 kcal per mol of the therapeutic agent. In some embodiments, the released heat is at least about 40 kcal per mol of the therapeutic agent and at most about 100 kcal per mol of the therapeutic agent. In some embodiments, the released heat is at least about 50 kcal per mol of the therapeutic agent and at most about 100 kcal per mol of the therapeutic agent. It should be appreciated that the amount of energy released per mol of the therapeutic agent can be determined by providing an appropriate ratio of heat generating reagents (e.g., first and second solutions or a liquid and a solid component) to the therapeutic agent. The heat or energy is released from mixing of the heat generating reagents (e.g., first and second solutions or a liquid and a solid component) as described herein. In some embodiments, the heat is reabsorbed in the dissolution of the dry medicament in the mixture.

In some embodiments, the solid component comprises a dry medicament as defined herein. In some embodiments, the solid component is separate from a dry medicament as defined herein.

In some embodiments, the liquid is one solvent. In some embodiments, the liquid is a solution comprising two or more solvents. In some embodiments, the liquid comprises a therapeutic agent as described herein. In some embodiments, the liquid comprises a non-therapeutic agent as described herein. In some embodiments, the liquid comprises a base as defined herein. In some embodiments, the liquid comprises an acid as described herein. In some embodiments, the liquid is an aqueous solution comprising a non-therapeutic agent. In some embodiments, the liquid is an aqueous solution comprising a base. In some embodiments, the liquid is an aqueous solution comprising an acid. In some embodiments, the liquid is an aqueous solution comprising a cosolvent (as defined herein) and a therapeutic agent. In some embodiments, the liquid is an aqueous solution comprising a cosolvent (as defined herein) and a non-therapeutic agent. In some embodiments, the liquid is an aqueous solution comprising a cosolvent (as defined herein) and a base. In some embodiments, the liquid is an aqueous solution comprising a cosolvent (as defined herein) and an acid.

In some embodiments, heat is released from mixing the solid component with the liquid. In some embodiments, heat is released from the exothermic reaction of mixing the solid component and the liquid. In some embodiments, the exothermic reaction involves a neutralization reaction involving combination of an acid and a base. For example, mixing a liquid comprising hydrochloric acid with a solid component comprising sodium hydroxide.

In some embodiments, the solid component is mixed with the liquid before the dry medicament is added. In some embodiments, the dry medicament is added to the solid component prior to mixing with the liquid.

It is understood that the provided methods can be applied to configurations such as traditional syringe, auto-injector (e.g., EpiPen), pumps, or infusion systems. The provided methods can also be practiced manually with vials. It is recognized that the configuration can have insulation to contain the heat generated in the mixing to promote solubility of the dry medicament.

In some embodiments, the inventive methods prepare medical solutions that can be delivered in injector devices. In some embodiments, the mixing is performed in an auto-injector prior to injection. In some embodiments, the mixing is performed in a prefilled syringe prior to injection. In some embodiments, an injector device also contains a liquid reservoir that can be accessed to deliver a fluid to the dry medicament in order to solubilize and/or rehydrate and/or dissolve the drug immediately prior to injection. In some embodiments, the injector is an auto-injector that automatically mixes the dry medicament with the fluid when the injector is activated.

In order that the invention described herein may be more fully understood, the exemplified auto-injector devices to practice the inventive methods are provided in FIGS. 1-11. It should be understood that these exemplified devices are for illustrative purposes only and are not to be construed as limiting this invention in any manner.

Figure 4:
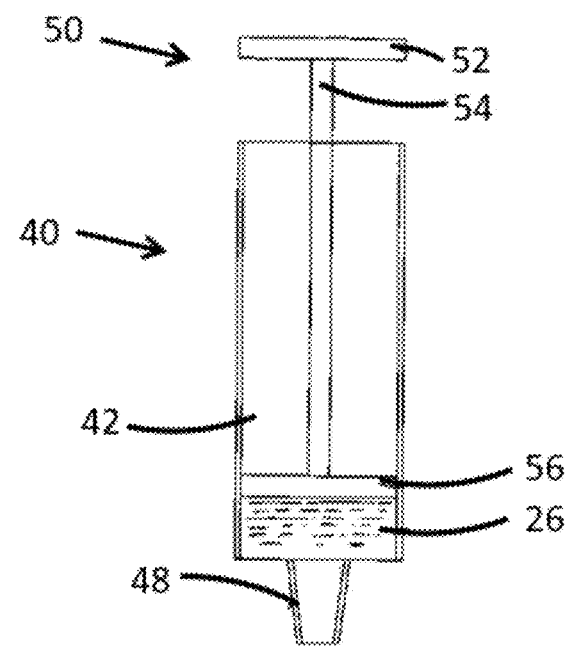
FIG. 4 shows a non-limiting embodiment of an injection system 20 using the inventive methods.
Figure 4:
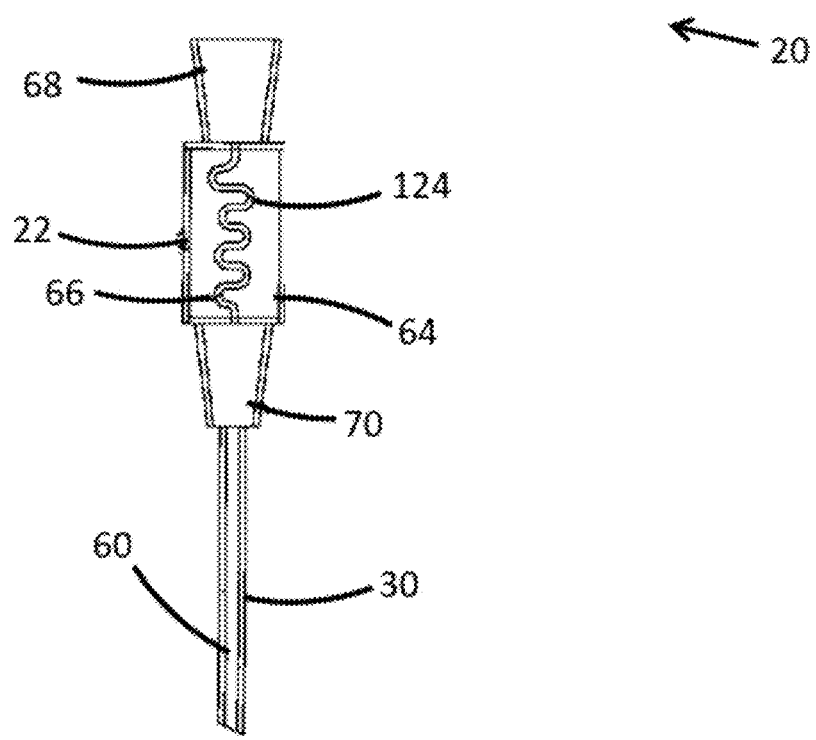

The inventive methods can be used in a device with a single mixing compartment, for example, in the form of a channel, conduit, or chamber (see FIG. 4). The single-mixing compartment serves to mix a first liquid, a second liquid, with a dry medicament to generate a solution. The single-mixing compartment can also serves to mix a liquid with a dry medicament to generate a solution. The inventive methods can also be practiced in a device with multiple mixing compartments, for example, two mixing compartments or three mixing compartments.

An exemplified injection system 20 (FIG. 4) has a syringe 40 and a mixture 22 for holding a dry medicament. The syringe 40 has a cylindrical tube 42 defining a volume 44. The cylindrical tube 42 of the syringe 40 tapers down to an outlet port 48. The syringe 40 has a plunger 50 with a depressing handle 52, a shaft 54, and a piston 56 for forcing the liquid component 26 out of the outlet port 48. The injector 30 is shown as a needle 60 as a part of the mixer 22 although it can be separate from the mixer 22. The injector 30 can also be a nozzle or tubing for delivery of the mixed combined medicament 28.

Another exemplified injection system (FIG. 4) having the mixer 22 with a housing 64 that defines an interior flow chamber 66 with an inlet 68 and an outlet 70. The mixer 22 with a single channel, such as a microchannel 124, is shown. The micro-channel 124 of the mixing device 22 is a serpentine channel, which defines a fluid pathway between the inlet 68 and the outlet 70. Fluid may enter in and out of the outlet 70 as well as the inlet 68. The serpentine channel 124 has two functions: the first function enables miniaturization of the channel structure by bending the fluid flow direction so that the channel can double back, thus a longer channel more efficiently utilizes a smaller area. The second function is that the natural flow becomes disrupted every time there is a bend or elbow in the channel, which results in mixing dependent on the cross section of the channel. In certain embodiments, the liquid, is pushed through the mixer 22 and out of the needle 60.

Figure 5A:
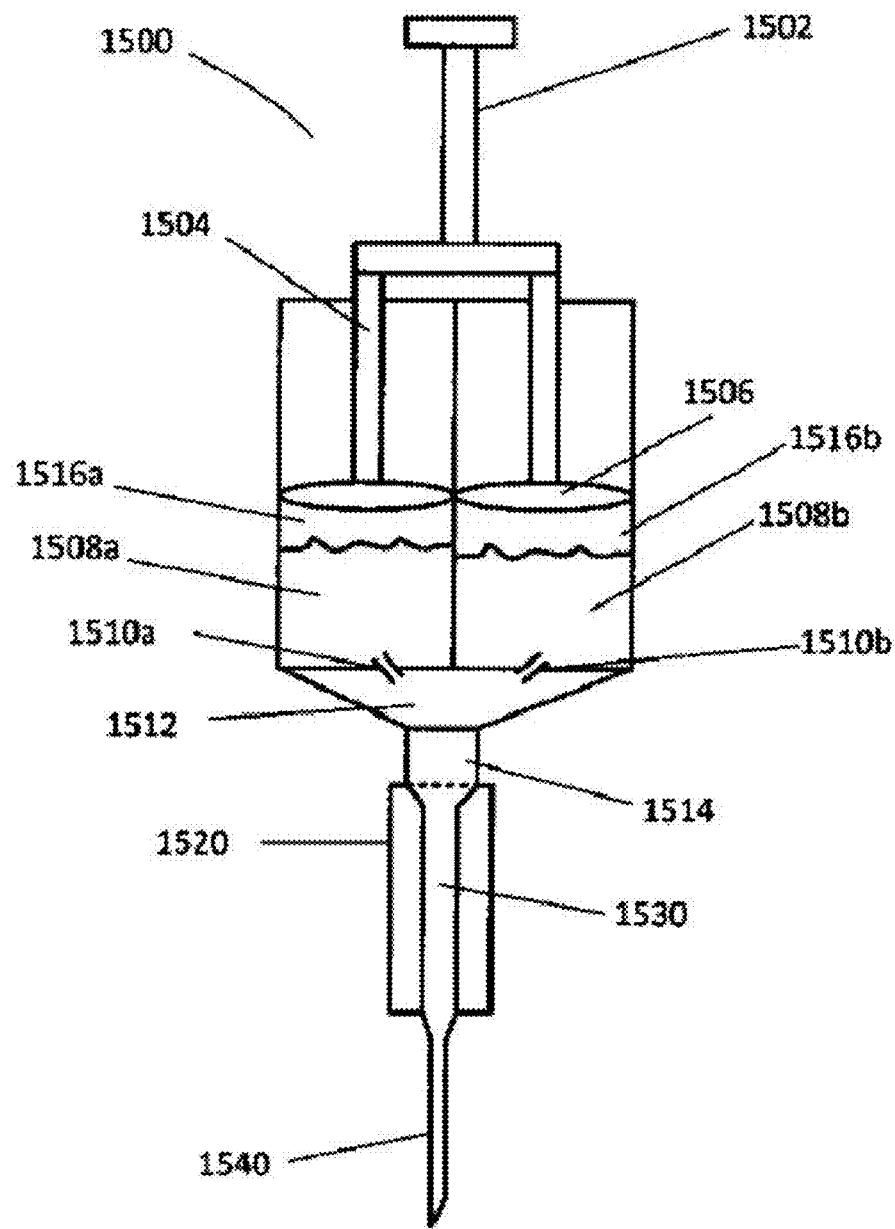
FIGS. 5A and 5B illustrate a non-limiting embodiment of a dual wet chamber injection device configured to hold the first liquid and the second liquid that combine to form an exothermic reaction to aid in dissolving the dry medicament in a fluidic channel.
Figure 5B:
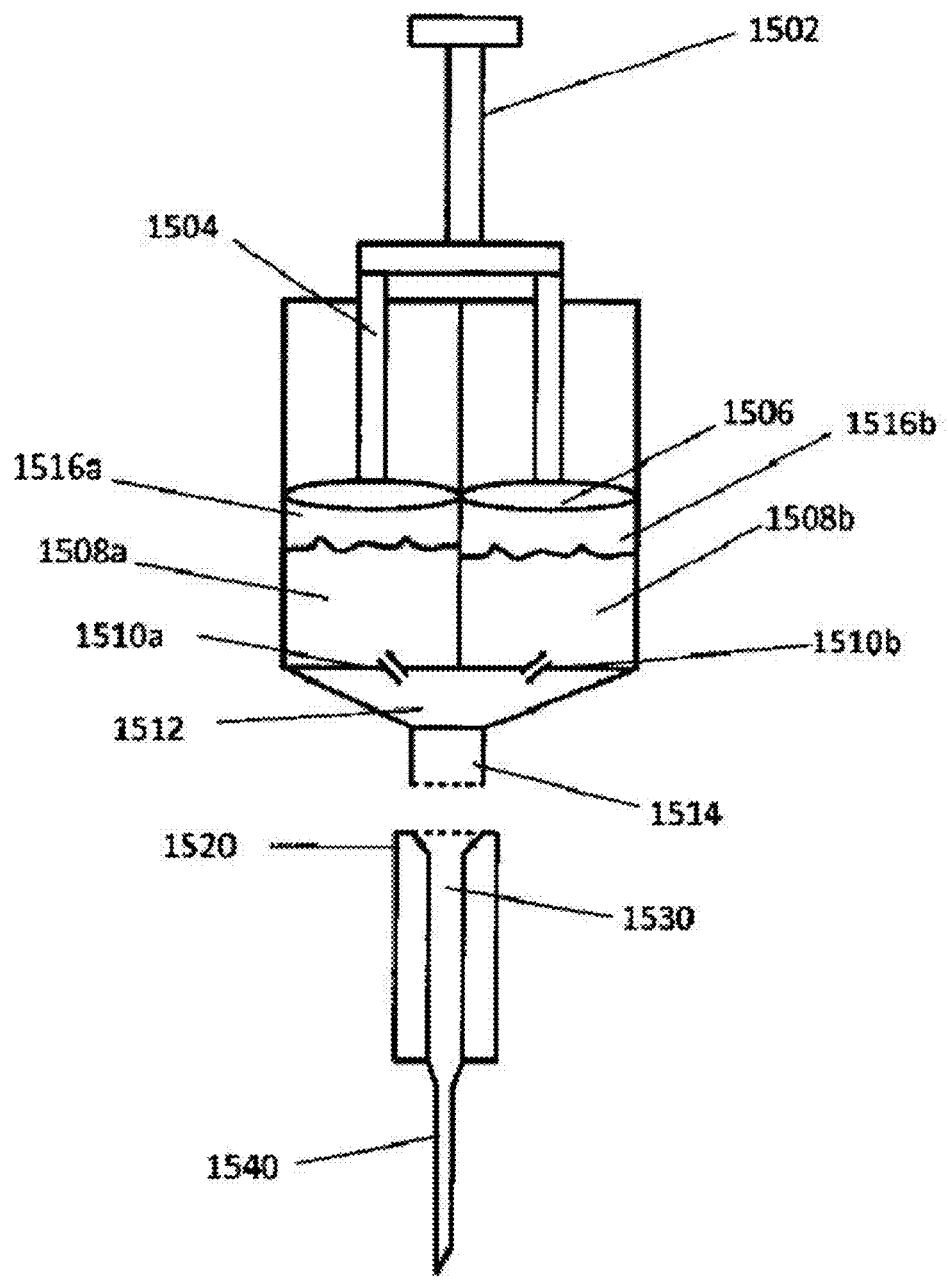

An exemplified dual-chamber device is shown in FIG. 5A and FIG. 5B. In one embodiment of the dual-chamber device, a first liquid and a second liquid can be mixed with a dry medicament concurrently or sequentially to generate a medical solution. In another embodiment of the dual-chamber device, a first liquid is mixed with a dry medicament, followed by addition of the second liquid. In another embodiment of the dual-chamber device, a second liquid is mixed with a dry medicament, followed by addition of the first liquid. In another embodiment of the dual-chamber device, a first liquid and a second liquid are mixed independently of the dry medicament. In some embodiments, the mixed liquids can be transferred to a chamber that contains the dry medicament, and in some embodiments the dry medicament can be added to a chamber that contains the mixed liquids, as aspects of the disclosure are not limited in this respect.

An exemplified injection system (FIG. 5A and 5B) 1500 has a pair of wet component containers 1516a and 1516b that contain a first liquid 1508a and a second liquid 1508b which are mixed together prior to mixing with a dry medicament. The syringe of the system 1500 has a plunger 1502 with a pair of shafts 1504 that each drive a plunger 1506 in a respective liquid component volume. As the respective liquid components 1508a and 1508b are pushed through their respective valve 1510a and 1510b, the two liquid components mix in a wet mixing volume 1512 where a liquid mixture is formed. As the plunger 1502 continues to push, the combined mixture flows through a fluidic channel 1530 of a mixer 1520 that contains the dry medicament. The combined medicament, which contains the dry medicament within the combined liquid mixture, flows through the needle 1540.

Figure 6:
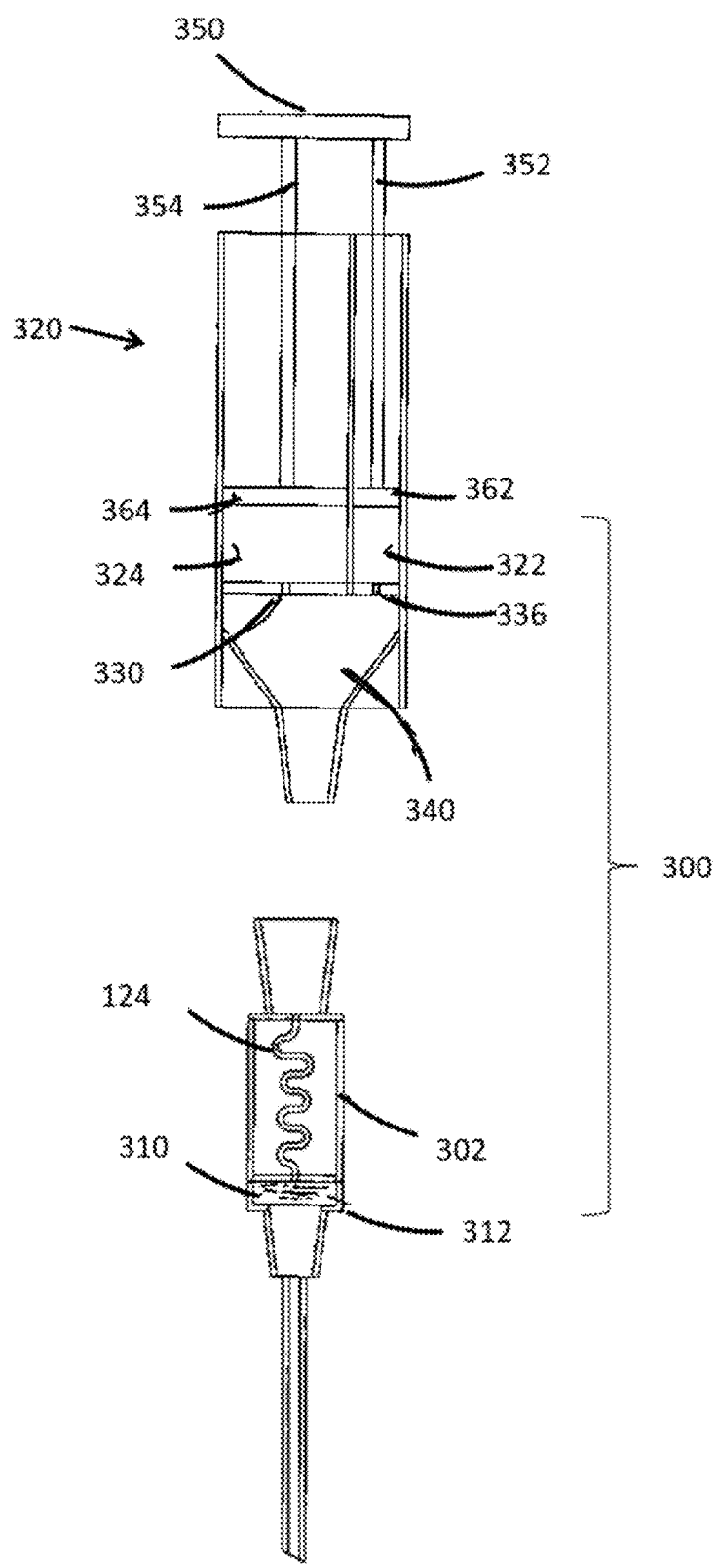
FIG. 6 shows a non-limiting embodiment of an injection system 300 using the inventive methods.
Figure 7:
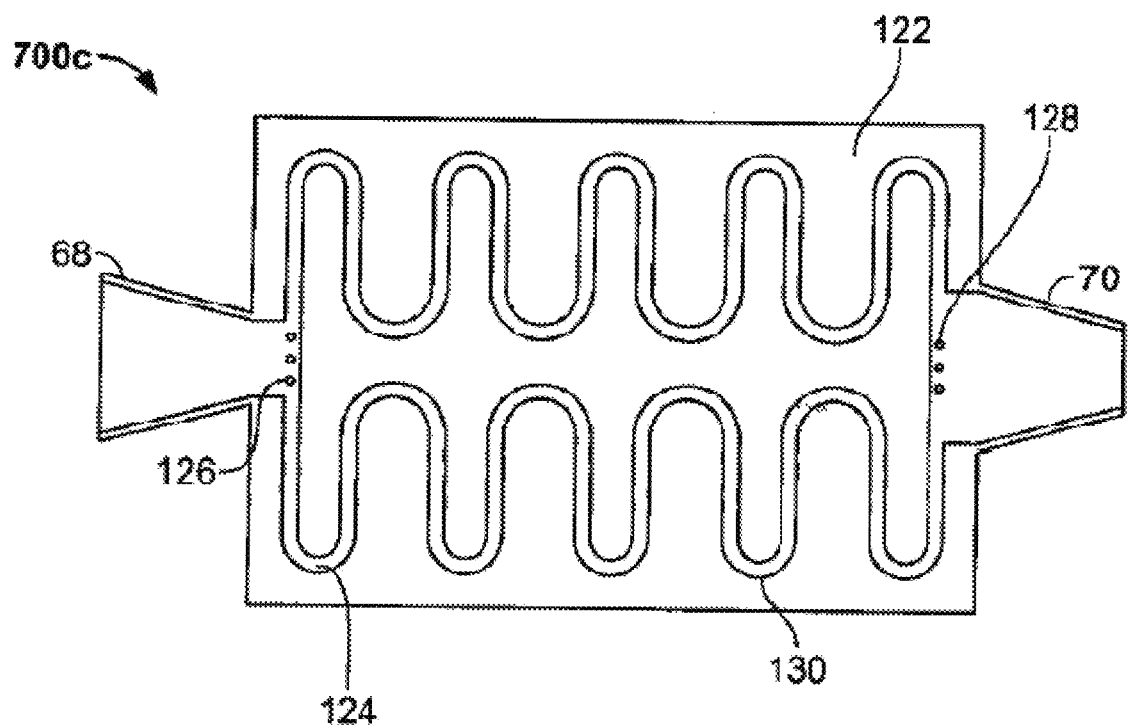
FIG. 7 is a non-limiting embodiment of a sectional view of an enlarged portion of an exemplified mixer.
Figure 8:
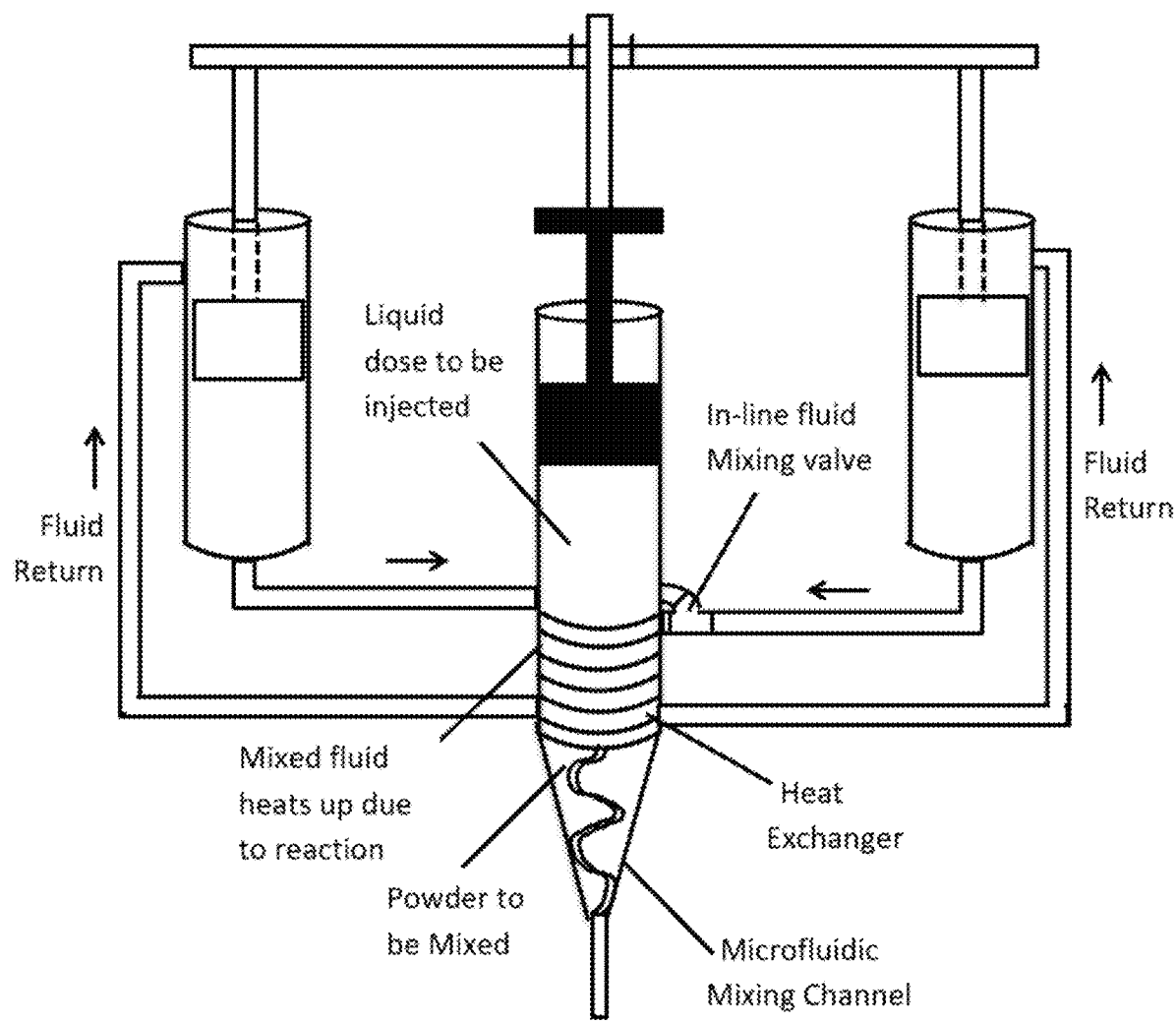
FIG. 8 shows a non-limiting embodiment of an injection device equipped with a heat exchanger in the form of the tube coil around the dry medicament vial. Heat may be activated via mixing multiple liquids and/or mixing at least one liquid with at least one solid component.
Figure 9:
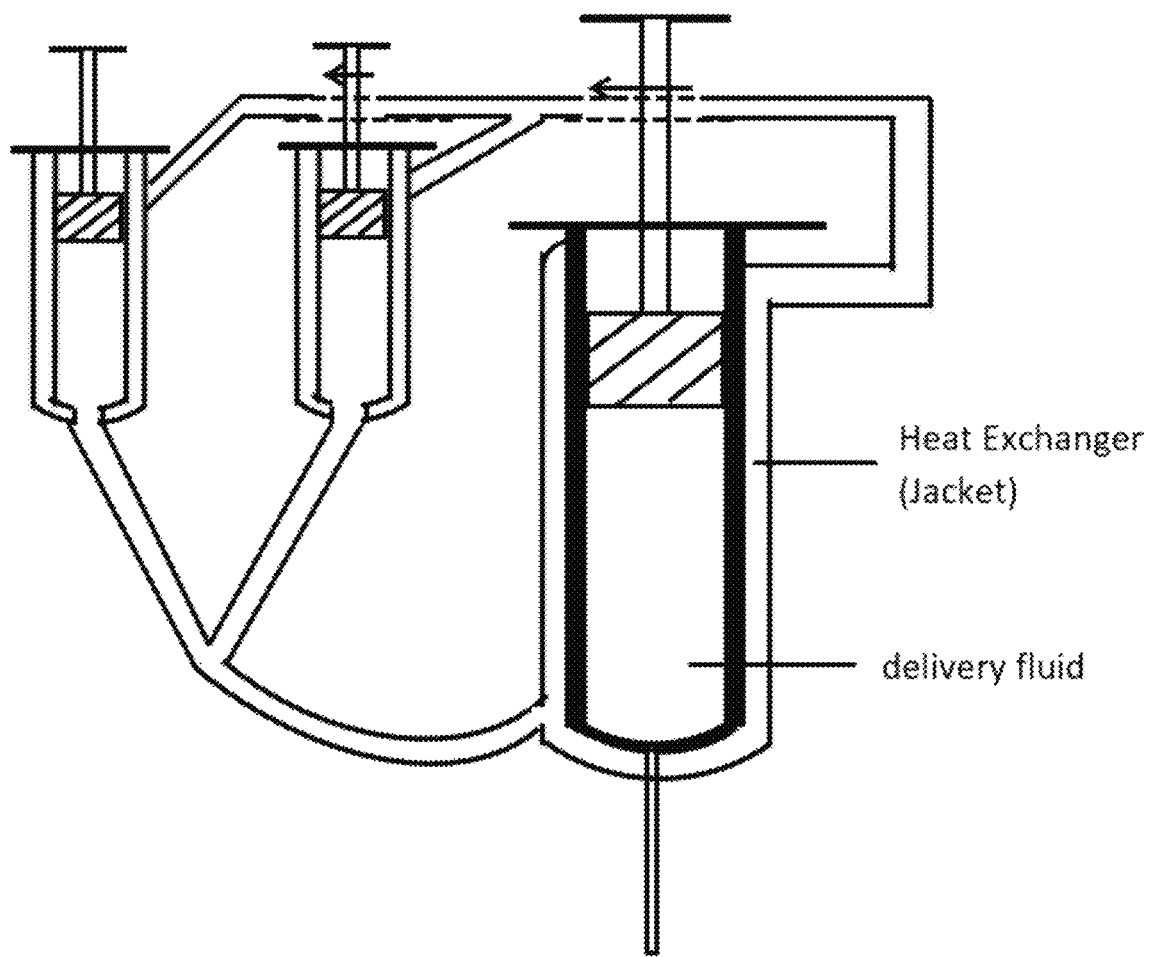
FIG. 9 shows a non-limiting embodiment of an injection device equipped with a heat exchanger having a jacket around the vial containing the dry medicament. Heat may be activated via mixing multiple liquids and/or mixing at least one liquid with at least one solid component.

An exemplified tri-chamber device is shown in FIG. 6. In one embodiment of a tri-chamber device, a first liquid, a second liquid, and a third liquid, can be mixed with a dry medicament concurrently or sequentially to generate a medical solution. In another embodiment of a tri-chamber device, a first liquid is mixed with a dry medicament, followed by addition of the second liquid and the third liquid. In another embodiment of a tri-chamber device, a second liquid is mixed with a dry medicament, followed by addition of the first liquid and the third liquid. In another embodiment of a tri-chamber device, a first liquid and a second liquid are mixed followed by addition of the dry medicament and subsequent addition of the third liquid. In another embodiment of a tri-chamber device, a first liquid, a second liquid, and a third liquid are mixed followed by addition of the dry medicament.

An exemplified injection system 300 (FIG. 6) has a mixer 302 with a container 310 for holding a third liquid 312. The system 300 has a syringe 320 having a pair of liquid component containers 322 and 324 that contain a first liquid 332 and a second liquid 334 which are mixed together prior to mixing with a dry medicament 24. The syringe 320 of the system 300 has a plunger 350 with a pair of shafts 352 and 354 that each drive a plunger 362 and 364 in a respective liquid volume. As the respective liquids 332 and 334 are pushed through their respective valves 336 and 338, the liquid components mix in a wet mixing volume 340 where a combined liquid mixture is formed. As the plunger 350 continues to push, the combined liquid mixture flows through a fluidic channel 124 of the mixer 302 that contains the dry medicament 24. The combined liquid mixture that mixes with the dry medicament 24 may have exothermic properties. This exothermic property may result in improved mixing with the dry medicament 24.

An exemplified drug mixing system 700 (FIG. 7) can have multiple conduits or channels and seals. The mixer 122 has an inlet 68 which opens into an inlet void 126. A plurality of channels 124 start at the inlet void 126 and end in an outlet void 128 at the outlet 70. Each of the channels 124 has a circuitous path 130 with various radiuses and chaos-inducing features. Each channel 124 can have variations in the cross sectional area and characteristics of the walls of the channel 124 to cause the flow of the liquid 26 to mix thoroughly with the dry medicament.

It is understood that the inventive methods can be practiced with a device where heat is provided externally. In some embodiments, heat is provided from an external heating system to a mixing device to practice the inventive methods. In some embodiments, heat is provided from an external irradiation system to a mixing device to practice the inventive methods. In some embodiments, heat is provided from an external pressure system to a mixing device to practice the inventive methods. In some embodiments, heat is provided from physical means such as rubbing to a mixing device to practice the inventive methods.

In some embodiments, heat is provided to dissolve the dry medicament by directly contacting the dry medicament with the first liquid and/or second liquid. In some embodiments, heat is provided to dissolve the dry medicament by directly contacting the dry medicament with a liquid and a solid component. In some embodiments, the heat is provided by an exothermic reaction between a first liquid and a second liquid or between a liquid and a solid component. However, it should be appreciated that in some embodiments, heat may be generated (e.g., in addition to or instead of) by an exothermic reaction between the dry medicament and one or more liquid and/or solid components that are mixed with the dry medicament.

In some embodiments, heat is provided to dissolve the dry medicament via a heat exchanger (e.g., from a source other than the mixture that contains the dry medicament). In certain embodiments, the heat exchanger is a microfluidic-scale heat exchanger. In some embodiment, the heat exchanger transfers heat from mixing the first liquid and second liquid to the dry medicament. In some embodiment, the heat exchanger transfers heat from mixing the liquid and the solid component to the dry medicament. In certain embodiments, the heat-generating components (e.g. the first liquid and the second liquid, or the liquid and the solid component) are stored in separate containers, and mix in separate channels from the medicament stream. In certain embodiments, the heat generating reaction is contained in a closed-loop system of the heat exchanger (see FIGS. 8-11). In some embodiments, the heat exchange is accomplished by heating the liquid storage vial prior to injection, or by heating the mixing channel via a microfluidic heat exchanger. Microfluidic heat exchange may increase the rate of heat transfer. In some embodiments, the closed loop system of the heat exchanger may also evolve a gas, or heat contained gas (such as air), which can be used to force the medicament injection process. In some embodiments, upon initiation of the heat-producing exothermic reaction, a byproduct from the reaction could be a gaseous species to increase the pressure on the backside of the reactant plungers shown in FIGS. 5-8. This gaseous byproduct would in turn provide infusion force on the medicament plunger and thus assure that injection is not made until heating has occurred and proper mixing of the medicament is possible.

In some embodiments, a nurse and/or doctor would take two vials: One of a dry medicament and one containing a solvent, for example, sterile water for injection. The nurse and/or doctor would then use a syringe to draw out the sterile water and subsequently dispense the water into the vial of the dry medicament. The nurse and/or doctor would then agitate the vial that now contains the water and the dry medicament until all the medicament is in a solution. The nurse and/or doctor would then draw the mixed and/or dissolved liquid dose of the medicament into a syringe and then inject the medical solution into the patient. In some embodiments, the injection is carried out prior to giving medication orally. In some embodiments, the injection is carried out prior to giving medication through I/V. In some embodiments, the injection is carried out prior to giving medication through the skin using a topical delivery mechanism and/or any other method of introducing drugs into a human and/or non-human where the compound would need to be reconstituted before delivery.

In some embodiments, the dry medicament is prepared by drying a drug solution e.g., by vacuum drying, freeze drying, lyophilizing, or any suitable drying technique. In some embodiments the dry drug is placed inside the autoinjector as a dry powder. In some embodiments, a dry medicament may have any suitable particle size that allows for efficient and rapid reconstitution. In some embodiments, the particle size of the dry medicament can be controlled by drying a drug solution within a confined volume. For example, in some embodiments, a drug solution is dried within the confines of a device, for example, an autoinjector. As a result, the particle size of a dried drug composition may be one the order of the diameter of a microfluidic channel (e.g., from about 1 micron to about 500 microns in diameter).

In some embodiments, the medical solution is administered to a human subject. In some embodiments, the medical solution is administered to a non-human subject.

In some embodiments, it should be appreciated that one or more components of any injection system or device described herein can be manufactured from any suitable material, for example materials that are acceptable for delivery of a medicament to a subject (e.g., a human subject). For example, one or more components (e.g., a chamber, vial, plunger, container, channel, tube, etc.) may be made of glass and/or biocompatible plastic or polymer and/or metal and/or any other acceptable material and or other materials acceptable by a regulatory body (such as the FDA) or other approved bodies. It also should be appreciated that in some embodiments one or more components of any injection system or device described herein are of a size suitable for preparing and/or injecting therapeutically acceptable volumes of medicament for delivery to a subject (e.g., a human subject). For example, one or more components (e.g., a chamber, vial, plunger, container, channel, tube, etc.) may be of a size suitable for containing, and/or preparing (e.g., mixing), and/or delivering (e.g., to a subject, for example a human subject) between 0.01 ml and 2 ml of solution, for example between 0.5 ml and 1 ml of solution, between 0.1 ml and 0.4 ml of solution, or around 0.1 ml, 0.2 ml, 0.3 ml, 0.4 ml, or 0.5 ml of solution.

In some embodiments, a dry composition described herein and/or exemplified herein retains greater than 90% potency, greater than 95% potency, between 90% and 100% potency, or between 90% and 115% potency when subjected to the following temperature exposure of less than −30° C., or between −30° C. and −25° C., or less than −25° C., or between −25° C. and −20° C., or less than −20° C., or between −20° C. and −15° C., or less than −15° C., or between −15° C. and −10° C., or less than −10° C., or between −10° C. and −5° C., or less than −5° C., or between −5° C. and 0° C., or less than 0° C., or between 0° C. and 5° C., or less than 5° C., or between 5° C. and 10° C., or less than 10° C., or between 10° C. and 15° C., or less than 15° C., or between 15° C. and 20° C. or less than 20° C. or between 20° C. and 25° C. or greater than 25° C., or between 25° C. and 30° C., or greater than 30° C. or between 30° C. and 35° C., or greater than 35° C., or between 35° C. and 40° C., or greater than 40° C., or between 40° C. and 45° C., or greater than 45° C., or between 45° C. and 50° C., or greater than 50° C., or between 50° C. and 55° C. or greater than 55° C., or between 55° C. and 60° C., or greater than 60° C. for up to 1 year, 2 years, 3 years, 5 years, 7 years, for up to 10 years or for greater than 10 years.

In some embodiments, after the L-epinephrine powder has been dissolved in an injector device, the resulting solution retains a potency greater than 90% potency, greater than 95% potency, between 90% and 100% potency, or between 90% and 115% potency even when the dry L-Epinephrine has been previously subject to a temperature exposure of less than −30° C., or between −30° C. and −25° C., or less than −25° C., or between −25° C. and −20° C., or less than −20° C., or between −20° C. and −15° C., or less than −15° C., or between −15° C. and −10° C., or less than −10° C., or between −10° C. and −5° C., or less than −5° C., or between −5° C. and 0° C., or less than 0° C., or between 0° C. and 5° C., or less than 5° C., or between 5° C. and 10° C., or less than 10° C., or between 10° C. and 15° C., or less than 15° C., or between 15° C. and 20° C. or less than 20° C. or between 20° C. and 25° C. or greater than 25° C., or between 25° C. and 30° C., or greater than 30° C. or between 30° C. and 35° C., or greater than 35° C., or between 35° C.

and 40° C., or greater than 40° C., or between 40° C. and 45° C., or greater than 45° C., or between 45° C. and 50° C., or greater than 50° C., or between 50° C. and 55° C. or greater than 55° C., or between 55° C. and 60° C., or greater than 60° C. for up to 1 year, 2 years, 3 years, 5 years, 7 years, for up to 10 years or for greater than 10 years.

In some embodiments, a dry composition described herein or exemplified in the Examples retains a chiral purity greater than 60%, greater than 70%, greater than 75%, greater than 80%, greater than 85%, greater than 90%, greater than 95%, 95% to 100%, L-Epinephrine when subject to a temperature exposure of less than −30° C., or between −30° C. and −25° C., or less than −25° C., or between −25° C. and −20° C., or less than −20° C., or between −20° C. and −15° C., or less than −15° C., or between −15° C. and −10° C., or less than −10° C., or between −10° C. and −5° C., or less than −5° C., or between −5° C. and 0° C., or less than 0° C., or between 0° C. and 5° C., or less than 5° C., or between 5° C. and 10° C., or less than 10° C., or between 10° C. and 15° C., or less than 15° C., or between 15° C. and 20° C. or less than 20° C. or between 20° C. and 25° C. or greater than 25° C., or between 25° C. and 30° C., or greater than 30° C. or between 30° C. and 35° C., or greater than 35° C., or between 35° C. and 40° C., or greater than 40° C., or between 40° C. and 45° C., or greater than 45° C., or between 45° C. and 50° C., or greater than 50° C., or between 50° C. and 55° C. or greater than 55° C., or between 55° C. and 60° C., or greater than 60° C. for up to 1 year, up to 2 years, up to 3 years, up to 5 years, up to 7 years, up to 10 years or for greater than 10 years.

In some embodiments, after the L-epinephrine powder has been dissolved in an injector device, the resulting solution retains a chiral purity greater than 60%, greater than 70%, greater than 75%, greater than 80%, greater than 85%, greater than 90%, greater than 95%, 95% to 100%, even when the dry L-Epinephrine has been previously subject to a temperature exposure of less than −30° C., or between −30° C. and −25° C., or less than −25° C., or between −25° C. and −20° C., or less than −20° C., or between −20° C. and −15° C., or less than −15° C., or between −15° C. and −10° C., or less than −10° C., or between −10° C. and −5° C., or less than −5° C., or between −5° C. and 0° C., or less than 0° C., or between 0° C. and 5° C., or less than 5° C., or between 5° C. and 10° C., or less than 10° C., or between 10° C. and 15° C., or less than 15° C., or between 15° C. and 20° C. or less than 20° C. or between 20° C. and 25° C. or greater than 25° C., or between 25° C. and 30° C., or greater than 30° C. or between 30° C. and 35° C., or greater than 35° C., or between 35° C. and 40° C., or greater than 40° C., or between 40° C. and 45° C., or greater than 45° C., or between 45° C. and 50° C., or greater than 50° C., or between 50° C. and 55° C. or greater than 55° C., or between 55° C. and 60° C., or greater than 60° C. for up to 1 year, up to 2 years, up to 3 years, up to 5 years, up to 7 years, up to 10 years or for greater than 10 years.

Equivalents and Scope

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of the group members are present in, employed in, or otherwise relevant to a given product or process.

Furthermore, the disclosure encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the disclosure, or aspects of the disclosure, is/are referred to as comprising particular elements and/or features, certain embodiments of the disclosure or aspects of the disclosure consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the disclosure, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present disclosure that falls within the prior art may be explicitly excluded from any one or more of the claims. Because such embodiments are deemed to be known to one of ordinary skill in the art, they may be excluded even if the exclusion is not set forth explicitly herein. Any particular embodiment of the disclosure can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present disclosure, as defined in the following claims.

The invention claimed is:
1. An autoinjector comprising:
   a dry chamber comprising a dry epinephrine composition; and
   a wet chamber comprising a liquid acid composition, wherein the dry chamber is sealed from the wet chamber prior to activation,
   wherein activation of the autoinjector results in mixing of the liquid acid composition from the wet chamber with the dry epinephrine composition from the dry chamber.

2. The autoinjector of claim 1, wherein the liquid acid composition comprises HCl, phosphoric acid, or sulfuric acid.

3. The autoinjector of claim 1, wherein the liquid acid is sterile.

4. The autoinjector of claim 1, wherein the liquid acid comprises one solvent.

5. The autoinjector of claim 1, wherein the liquid acid comprises water.

6. The autoinjector of claim 5, wherein the liquid acid comprises water and an acid.

7. The autoinjector of claim 1, wherein the liquid acid has a pH from 0.1 to 6.0.

8. The autoinjector of claim 1, wherein the liquid acid has a pH from 0.5 to 5.0.

9. The autoinjector of claim 1, wherein the dry epinephrine forms a readily solubilized salt upon mixing with the liquid acid.

10. The autoinjector of claim 1, wherein the dry epinephrine is an epinephrine free base.

11. The autoinjector of claim 10, wherein the epinephrine free base is L-epinephrine free base.

12. The autoinjector of claim 1, wherein the dry epinephrine is an epinephrine salt.

13. The autoinjector of claim 12, wherein the epinephrine salt is a maleate, malate, fumarate, tartrate, bitartrate, sulfate, hydrochloride, or borate salt of epinephrine.

* * * * *